United States Patent
von Chamier-Glisczinski et al.

(10) Patent No.: US 10,151,707 B2
(45) Date of Patent: Dec. 11, 2018

(54) METHOD FOR THE SPECTRAL ANALYSIS OF SAMPLES BY MEANS OF A GRAPHITE TUBE

(71) Applicant: Analytik Jena AG, Jena (DE)

(72) Inventors: Robert von Chamier-Glisczinski, Jena (DE); Eike Thamm, Stadtroda (DE)

(73) Assignee: Analytik Jena AG, Jena (DE)

( * ) Notice: Subject to any disclaimer, the term of this patent is extended or adjusted under 35 U.S.C. 154(b) by 0 days.

(21) Appl. No.: 15/292,811

(22) Filed: Oct. 13, 2016

(65) Prior Publication Data

US 2017/0108450 A1 Apr. 20, 2017

(30) Foreign Application Priority Data

Oct. 14, 2015 (DE) .................. 10 2015 117 384

(51) Int. Cl.
*G06K 9/00* (2006.01)
*G01N 21/954* (2006.01)
(Continued)

(52) U.S. Cl.
CPC ............ *G01N 21/954* (2013.01); *G01N 1/44* (2013.01); *G01N 21/8851* (2013.01); *G06K 9/38* (2013.01);
(Continued)

(58) Field of Classification Search
CPC .... G01N 1/44; G01N 21/8851; G01N 21/954; G06K 9/38; G06K 9/4661; G06K 9/64; G06T 5/10; G06T 7/0044; G06T 7/602
See application file for complete search history.

(56) References Cited

U.S. PATENT DOCUMENTS

| | | |
|---|---|---|
| 3,730,630 A | 5/1973 | Witte |
| 4,824,241 A | 4/1989 | Littlejohn et al. |
| 2008/0088836 A1 | 4/2008 | Senn et al. |

FOREIGN PATENT DOCUMENTS

| | | |
|---|---|---|
| DE | 3876018 T2 | 11/1992 |
| EP | 0296480 B1 | 11/1992 |
| GB | 2286243 A | 9/1995 |

OTHER PUBLICATIONS

Barth, P., et al. "Determination of trace impurities in boron nitride by graphite furnace atomic absorption spectrometry and electrothermal vaporization inductively coupled plasma optical emission spectrometry using solid sampling." Spectrochimica Acta Part B: Atomic Spectroscopy 62.9 (2007): 924-932. (Year: 2007).*

(Continued)

*Primary Examiner* — Nirav G Patel
(74) *Attorney, Agent, or Firm* — Christopher R. Powers; PatServe

(57) ABSTRACT

A method for the spectral analysis of samples in a graphite tube, comprising the steps of: inserting a liquid sample into a graphite tube; drying the sample by heating the graphite tube; transferring the sample into a particle cloud by further heating up the graphite tube; and measuring one of the optical signals influenced or generated by the sample with a detector; wherein image sequences of the interior of the graphite tube are recorded with a two-dimensional camera having a plurality of image elements over selected periods of time during the spectral analysis; is characterized in that the images of the image sequences are automatically processed with image processing methods, wherein a reference image of the interior of the graphite tube is determined; and the condition of the graphite tube, of the sample and/or of a dosing means for inserting the sample into the graphite tube is determined by comparison of the images of the image sequences to the reference image.

17 Claims, 13 Drawing Sheets

(51) Int. Cl.
- *G06K 9/64* (2006.01)
- *G06K 9/38* (2006.01)
- *G06K 9/46* (2006.01)
- *G06T 7/60* (2017.01)
- *G06T 5/10* (2006.01)
- *G06T 7/00* (2017.01)
- *G01N 21/88* (2006.01)
- *G01N 1/44* (2006.01)

(52) U.S. Cl.
CPC ............ *G06K 9/4661* (2013.01); *G06K 9/64* (2013.01); *G06T 5/10* (2013.01); *G06T 7/0044* (2013.01); *G06T 7/602* (2013.01)

(56) References Cited

OTHER PUBLICATIONS

Boulo, Philippe R., et al. "Use of image processing to aid furnace set-up in electrothermal atomic absorption spectrometry." Journal of Analytical Atomic Spectrometry 12.3 (1997): 293-300. (Year: 1997).*

Phillippe R. Boulo et al.; "Use of Image Processing to Aid Furnace Set-up in Electrothermal Atomic Absorption Spectrometry"; Journal of Analytical Atomic Spectrometry; Mar. 1997; pp. 293-300; vol. 12; Signal Processing Division, Department of Electronics and Electrical Engineering, University of Strathclyde, Glasgow, United Kingdom; Department of Pure and Applied Chemistry, University of Strathclyde, Glasgow United Kingdom; Unicam Atomic Absorption, York Street, Cambridge, United Kingdom.

Jacobs, David W.: Blob Detection. University of Maryland. Version: 2012. Online; Nov. 27, 2012. 11 pages.

Kaspers, Anne: Blob Detection. UMC Utrecht. Version: 2011. Online; Jan. 4, 2013. 14 pages.

Lowe, David G.: Distinctive Image Features from Scale-Invariant Keypoints. Version: Jan. 2004. Online; Jan. 16, 2013. 28 pages.

Shene, Ching-Kuang: Auto Focus. Version: Apr. 2004. Online; Nov. 10, 2012. 3 pages.

Wikimedia Foundation Inc.: Scale-invariant feature transform. Version: Jan. 2013. Online; Jan. 28, 2013. 16 pages.

Yokono, Jerry J.; Tomaso Poggio: Rotation Invariant Object Recognition from One Training Example. Massachusetts Institute of Technology. Version: Apr. 2004. Online; Feb. 1, 2013. 16 pages.

Glebov, Roman: Verfahren zum effzienten Tracking schneller Objekte—implementiert mit CUDA am Beispiel Tischtennis spielender Roboter. Hochschule fur Technik Stuttgart. Version: Dezember 2008.Online; 10-Okttober-2012. 124 pages.

Gremse, Felix: Skaleninvariante Merkmalstransformation—SIFT Merkmale. Rheinisch-Westfälischen Technischen Hochschule Aachen. Version: Januar 2006. Online: 22-Februar-2013. 16 pages.

Helmers, Henner: Autofokus. Version: 2013. Online; 14-März-2013. 7 pages.

Jung, Frank: Objekterkennung mit SIFT-Features. Version: Sep. 2006. Online; 28-Januar-2013. 59 pages.

* cited by examiner

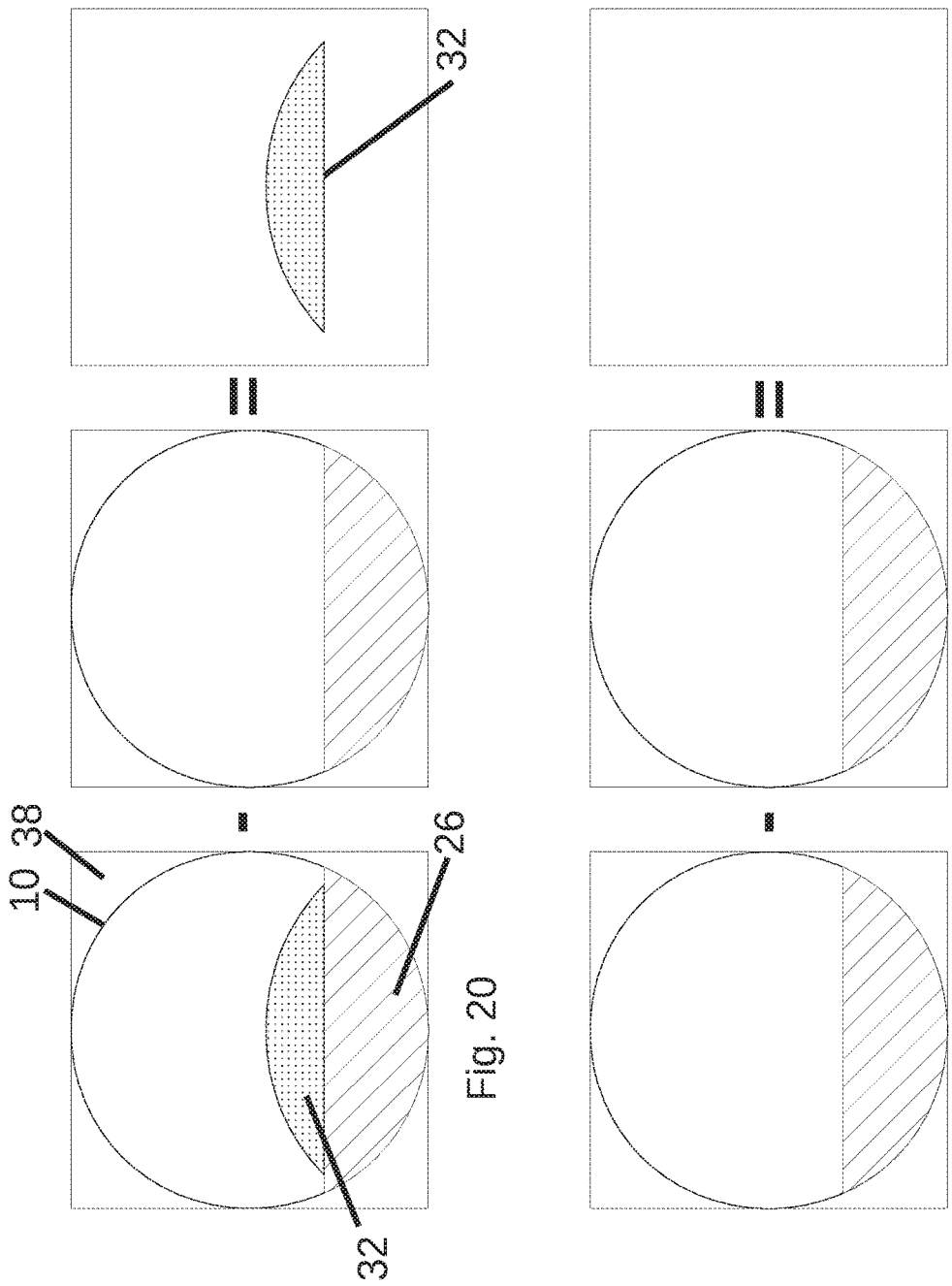

$h_X$

| -1 | 0 | +1 |
|---|---|---|
| -2 | 0 | +2 |
| -1 | 0 | +1 |

$h_Y$

| +1 | +2 | +1 |
|---|---|---|
| 0 | 0 | 0 |
| -1 | -2 | -1 |

Fig. 36

METHOD FOR THE SPECTRAL ANALYSIS OF SAMPLES BY MEANS OF A GRAPHITE TUBE

TECHNICAL FIELD

The invention relates to a method for the spectral analysis of samples in a graphite tube also referred to as an electrothermal atomizer, comprising the steps of:
(a) inserting a liquid sample into a graphite tube;
(b) drying the sample by heating the graphite tube;
(c) transferring the sample into a particle cloud by further heating up the graphite tube; and
(d) measuring one of the optical signals influenced or generated by the sample with a detector;
wherein
(e) image sequences of the interior of the graphite tube are recorded with a two-dimensional camera having a plurality of image elements over selected periods of time during the spectral analysis.

With such a method atomic absorption spectrometers, for example, are operated in order to very precisely determine the quantity of an element in a sample.

With such a method, the usually liquid sample is dosed in a graphite tube. A pipette or an autosampler is used for this purpose. The graphite tube is heated step-wise to different temperatures according to a temperature program. Here, the graphite tube is first heated to a relatively low temperature, where the sample is dried and the analytically uninteresting solvent is vaporized. Then, the graphite tube with the dried sample is brought up to a high temperature, typically above 1400° C. The sample vaporizes into a particle cloud. During pyrolysis molecules are split into atoms by these high temperatures. The particle cloud is optically examined with regard to its spectral characteristics, for example by fluorescence, absorption or emission measurements.

Particularly good analytical results are achieved by means of a L'vov platform in a tubular graphite tube based on the STPF-concept.

The selected temperature program for heating the graphite tube has a large influence on important analytical characteristics of the measurement, especially on accuracy, sensitivity and detection limit. In order to obtain good results, it is necessary to ensure that the sample is fully dried but the components that are to be examined are not yet vaporizing. The sample must not splash or escape too early out of the dosage hole of the graphite tube. Different samples, therefore, require a different temperature program.

In addition to the temperature program, the dosing accuracy of the autosampler or the pipette is also important. Depending on whether samples are placed at different points in the graphite tube, the measurement results may vary. In order to obtain high accuracy and reproducibility, the sample positioning is monitored.

The development of methods is understood, among other things, as the development of temperature programs and additives for various samples.

PRIOR ART

DE 3876018 T2 describes the structure and mode of operation of a typical graphite tube in an atomic absorption spectrometer, where the duration of the temperature program should be shortened by spraying the sample from a tube into the preheated graphite tube.

An atomic absorption spectrometer is offered under the mark contrAA® 600 on the website http://www.anayltik-jena.de/de/analytical-instrumentation/produkte/atomabsorptionsspektrometer/hs-cs-aas/contraar-600.html which uses an integrated camera for observing the deposition of droplets and drying in the graphite tube. It is disclosed that due to the integrated color camera, all processes in the graphite tube can be observed in great detail, from the deposition of droplets to the drying and pyrolysis. According to this, the easy and correct method development is supposed to be possible.

An exemplary temperature program is described on www.wikipedia.de:
1. Drying 1: the graphite tube is heated up to a temperature of 90° C. to 130° C. for approximately 30 s in order to narrow down and virtually dry the sample.
2. Drying 2: the graphite tube is heated up to a temperature of 400° C. for approximately 20 s in order to fully dry the sample (if crystal water was present)
3. Pyrolysis: the graphite tube is heated up to a temperature of 400° C. to 1500° C. (depending on the element) for approximately 30 s in order to remove organic components. This is effected by pyrolysis or incineration.
4. Atomization: the sample is atomized at 1500° C. to 2500° C. (depending on the element specific atomizing temperature) for approximately 5 s.
5. Cleaning out: finally, after the end of the analysis, it is heated up to a temperature of 2500° C. (transversely heated graphite tube) to 2800° C. (longitudinally heated graphite tube) for approximately 3 s in order to atomize remainders of the sample.

The dry times are, thereby, fixed in every temperature program. Further prior art is:
Glebov, Roman: Verfahren zum effzienten Tracking schneller Objekte—implementiert mit CUDA am Beispiel Tischtennis spielender Roboter. Hochschule fur Technik Stuttgart. http://glebov.de/static/papers/bthes.pdf. Version: Dezember 2008.—[Online; 10-Oktober-2012]
Gremse, Felix: Skaleninvariante Merkmalstransformation—SIFT Merkmale. Rheinisch-Westfälischen Technischen Hochschule Aachen. http://ganymed. imib.rwth-aachen.de/lehmann/seminare/bv_2005-08.pdf. Version: Januar 2006.—[Online; 22-Februar-2013]
Helmers, Henner: Autofokus. http://www.henner.info/focus.htm. Version: 2013.—[Online; 14-März-2013]
Jacobs, David W.: Blob Detection. University of Maryland. http://www.cs.umd.edu/~djacobs/CMSC426/Blob.pdf. Version: 2012.—[Online; 27-November-2012]
Jung, Frank: Objekterkennung mit SIFT-Features. http://www.multimedia-computing.de/mediawiki/images/e/ea/BA_FrankJung.pdf. Version: September 2006.—[Online; 28-Januar-2013]
Kaspers, Anne: Blob Detection. UMC Utrecht. http://igitur-archive.library.uu.nl/student-theses/2011-0505-200339/Blob%20detection%20Final %20version.pdf. Version: 2011.—[Online; 04-Januar-2013]
Lowe, David G.: Distinctive Image Features from Scale-Invariant Keypoints. http://www.cs.ubc.ca/~lowe/papers/ijcv04.pdf. Version: Januar 2004. —[Online; 16-Januar-2013]
Shene, Ching-Kuang: Auto Focus. http://www.cs.mtu.edu/~shene/DigiCam/User-Guide/5700/AUTO-FOCUS/Auto-Focus.html. Version: April 2004.—[Online; 10-November-2012]
Wikimedia Foundation Inc.: Scale-invariant feature transform. http://en.wikipedia.org/w/index.php?title=Scale-invariant_feature_transform&oldid=533540415. Version: Januar 2013.—[Online; 28-Januar-2013]

Yokono, Jerry J.; Poggio, Tomaso: Rotation Invariant Object Recognition from One Training Example. Massachusetts Institute of Technology. http://cbcl.mit.edu/publications/ai-publications/2004/AIM-2004-010.pdf. Version: April 2004.—[Online; 01-Februar-2013]

DISCLOSURE OF THE INVENTION

It is an object of the invention to provide a method of the above mentioned kind, wherein a higher accuracy and reproducibility of the measurement is reached and the duration of the temperature program can be optimized independently from the sample.

According to the invention, this object is achieved for a method of the above mentioned kind in that
(f) the images of the image sequences are automatically processed with image processing methods,
(g) wherein a reference image of the interior of the graphite tube is determined; and
(h) the condition of the graphite tube, of the sample and/or of a dosing means for inserting the sample into the graphite tube is determined by comparison of the images of the image sequences to the reference image.

It is understood that further reference values extracted thereof can also be determined and processed. Every cuvette which can be heated up to high temperatures is understood here as a graphite tube. While cuvettes usually consist of graphite, what they are named after, it is also possible to use other materials, such as tantalum, tungsten or glass-like carbon.

A graphite tube includes, in addition to the actual tube, further components such as electric connections and the like. The term spectral analysis also includes the measurement of absorption, emission and fluorescence over all wavelength ranges for various wavelengths, both simultaneously or successively. While with the classic atomic absorption spectrometers only atoms are measured on their resonance wavelengths, it is also possible with CSAAS to detect ions and smaller molecules with the measurement. Accordingly, the term particle cloud is understood to mean all particles, especially atoms, ions, molecules and molecular fragments.

According to the invention a reference image is created by automatic processing. The reference image can be newly created for every measurement, for example, before the sample is inserted. However, it can also be determined by previous measurements and, for example, be saved for further use. In a comparison, a difference of the values is usually constructed on the basis of single image points. However, it is also possible to carry out the comparison by calculating the quotient or calculating the difference based on previous image processing, for example, in the frequency domain after a fourier transformation. For this purpose, computers or other data processing devices are used as image processing means. The data can be evaluated directly during the measurement process, for example, as a basis for a control loop. It is also possible, however, to evaluate the data separately and use it in following measurement processes within the scope of the development of methods, for example, in an assistance system. The dosing means for liquid samples are, in particular, pipettes and autosamplers. However, a spatula or a platelet may also be used for solid matter dosing, which is inserted with the sample.

In an assistance system, a user is assisted with the operation and measurement processes of a device, for example, of an atomic absorption spectrometer. It provides optimized parameters and values for the analysis procedure/-process, which the user may use. Moreover, the method according to the invention can form the basis of a control loop.

According to the invention, an image sequence consisting of images of the graphite tube is automatically recorded and each or several of the images are compared to the reference image. The comparison can determine the time when the desired condition is reached. Such a condition can, for example, be the time when the sample is fully dried. However, the comparison can also determine a time when a certain condition ceases to exist. Such a condition is reached, for example, when the dosing means is no longer located in the range of the graphite tube. It can further be determined, what kind of state it is. For example, the pipetting distance of the dosing means or the positioning of a platform can be determined.

The automatic processing enables the processing for all measurements. Thus, analytical outliers can be better interpreted and disregarded where applicable. Preferably, a following step of the spectral analysis is triggered when a selected target state is reached. Such a condition is the end of the dosing process or the termination of the drying. With known temperature programs drying was always effected over a set time period. This time period needs to be long enough in order to ensure that the sample is really fully dried. As a result, a safety time period was attached. With the method according to the invention, the end of the drying is readily determined and the next step can follow immediately. As a result, a safety time period is not required. The entire duration of the temperature program can, therefore, be shortened and the temperature can be controlled according to the condition of the sample.

Preferably, the images of the image sequences are processed only for one section which is the same for all images of the image sequences. This section is determined by filtering the underlying image at the beginning using an edge detector, for example, in the form of a Sobel filter or a high pass filter. Subsequently, it can be determined whether the intensity values in the filtered image have a deviation from an average or another fixed value that is larger than a threshold value. Regions with no changes and for which the intensity values are, therefore, smaller than an average value or threshold value, do not need to be processed. As a result, the data volume is reduced and the processing time is shortened.

In a preferred embodiment of the invention the position of the graphite tube or the position of parts of the graphite tube or the position of a platform arranged in the graphite tube, are automatically determined with the image processing means. However, it is also possible to save the position of the graphite tube and use it again for further measurements.

In a preferred embodiment of the invention the position and/or the pipetting distance of a dosing means for the insertion of the sample into the graphite tube is automatically determined with the image processing means. This ability can be used to help the user to adjust the suitable pipetting distance by means of the assistance system. The adjustment of the pipetting distance is necessary so that the dosing means does not collide against the graphite tube bottom or the pipetting distance is too big. Moreover, the pipetting distance is dependent on the sample.

Furthermore, it can be provided that the presence and/or the positioning of bubbles during the drying of the sample is automatically determined with the image processing means. This enables the recognition of a potentially falsely adjusted drying temperature.

Additionally, the invention may provide that the reaching of the complete drying of the sample is automatically determined with the image processing means.

An embodiment of the invention is described below in greater detail with reference to the accompanying drawings.

BRIEF DESCRIPTION OF THE DRAWINGS

FIG. 20 illustrates how the condition of the not yet dried sample is determined by calculating the difference between a reference image of the graphite tube and a current image of the graphite tube with a sample.

FIG. 21 illustrates how the reaching of the completed drying process is determined by calculating the difference between a reference image of the empty graphite tube and a current image of the graphite tube with a sample.

FIG. 36 illustrates a first ($h_x$) and a second ($h_y$) application of a Sobel operator according to the present disclosure.

DESCRIPTION OF THE EMBODIMENT

Figure 1:
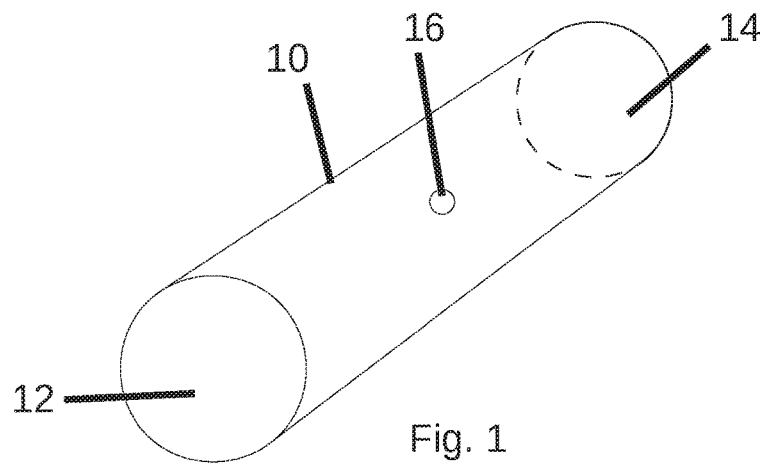
FIG. 1 is a schematic view of a graphite tube.

FIG. 1 shows a graphite tube generally designated with numeral 10. In the present embodiment, the graphite tube consists of graphite. Occasionally, however, graphite tubes of other materials are also used despite its name. The graphite tube is cylindrical and has two lateral openings 12 and 14. An opening 16 for the insertion of samples is provided about in the center of the range of the lateral surface. The liquid samples may be inserted manually, for example, with a pipette or automatically with an autosampler through the opening 16 into the interior of the graphite tube 10.

Figure 2:
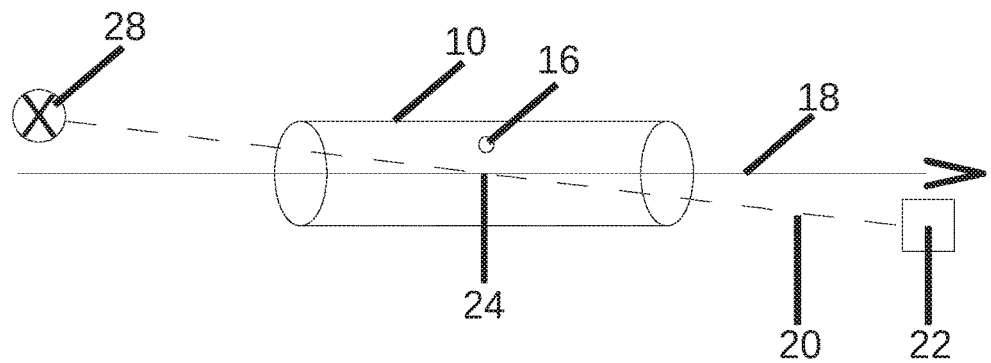
FIG. 2 illustrates the position of the camera with respect to the graphite tube in an atomic absorption spectrometer.

The graphite tube 10 is provided in the optical path 18 of an atomic absorption spectrometer or of another analytical device that works with a graphite tube. This is shown in FIG. 2. Atomic absorption spectrometers are well-known and, therefore, do not need to be illustrated nor described here any further. The graphite tube 10 is electrically heated up step-wise to high temperatures so that the inserted sample vaporizes to a particle cloud of ions, atoms and molecules. In addition to kind, quantity and composition of the samples, the form and duration of state of the particle cloud also depends on, among other things, the condition of the graphite tube during the analysis, the temperature program and the position of the sample and the pipetting distance of the autosampler, for example, of the pipette. In other words: the accuracy and the reproducibility of the measurement results depend on how reliably the sample is inserted and how well the process, with which the particle cloud is created, can be controlled.

For this purpose, it is known to provide a camera 22 in the device for observing the processes in the graphite tube. This is illustrated in FIG. 2. The camera 22 is positioned at an angle, so that the optical path 20 of the camera 22 does not otherwise influence the optical path 18 of the spectrometer. Furthermore, a LED light 28 is provided for illuminating the interior of the graphite tube 10. The optical path 20 of the camera 22 is designed in a way that it has its focus at the point 24 in the center of the graphite tube 10 below the opening 16.

Figure 3:
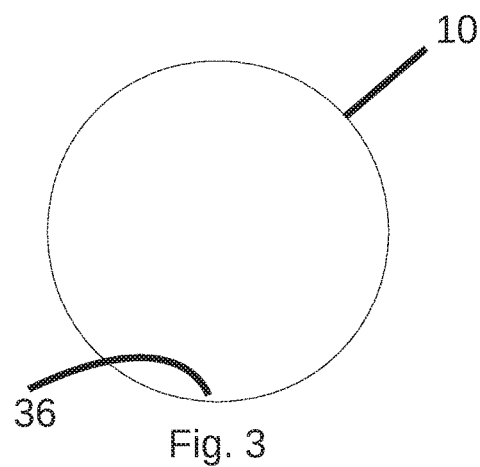
FIG. 3 is a cross section of a graphite tube without a platform.
Figure 4:
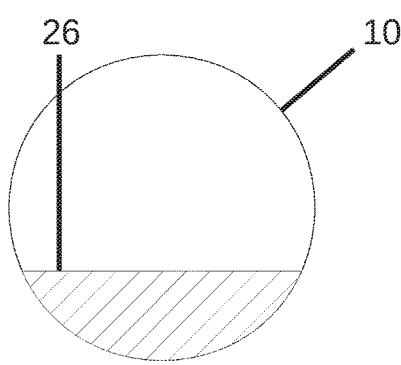
FIG. 4 is a cross section of a graphite tube with a platform.
Figure 5:
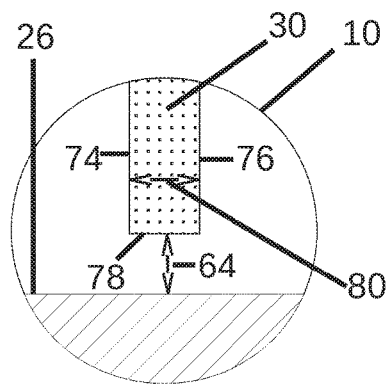
FIG. 5 is a cross section of the graphite tube of FIG. 4 with an inserted pipette, but not yet with a sample.
Figure 6:
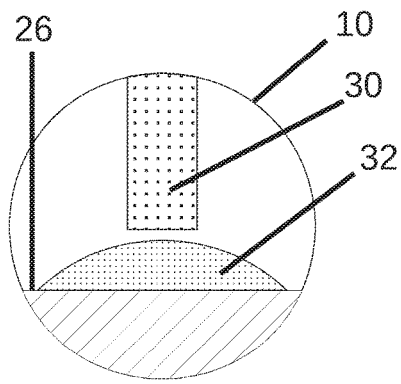
FIG. 6 is a cross section of the graphite tube of FIG. 4 during the deposition of the sample with a pipette.
Figure 7:
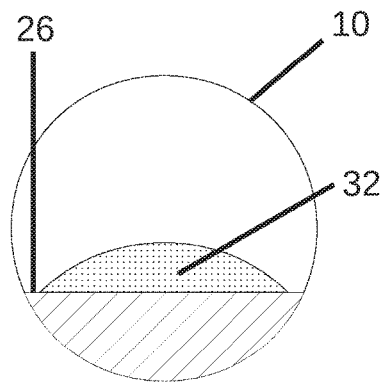
FIG. 7 is a cross section of the graphite tube of FIG. 4 with a deposited sample.
Figure 8:
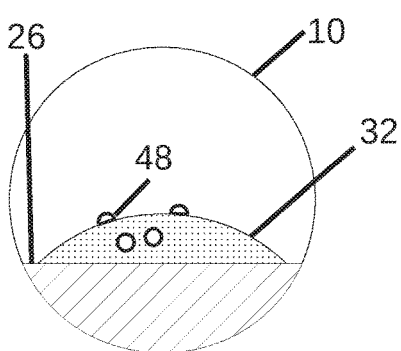
FIG. 8 is a cross section of the graphite tube of FIG. 4 during the drying process with bubble formation.
Figure 9:
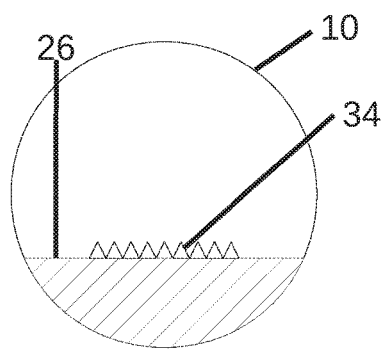
FIG. 9 is a cross section of the graphite tube of FIG. 4 with a dried sample.

FIG. 3 shows a cross section of a graphite tube without a platform and FIG. 4 shows a cross section of a graphite tube 10 with a L'vov platform 26. FIG. 5 and FIG. 6 schematically illustrate how a pipette 30 deposits a droplet 32 on the platform 26. Then, the pipette 30 is removed again. The situation with liquid droplets is illustrated in FIG. 7. After the dosage, the graphite tube 10 is heated in the well-known way. The sample 32 is dried. Bubbles 48, which are illustrated in FIG. 8, may form during the drying step. The droplet 32, illustrated in liquid form in FIG. 6 and FIG. 7, is shown in FIG. 9 after the drying but before the formation of the particle cloud during the atomization. The sample 34 only consists of a few solid components. Similarly to the graphite tubes 10 with platform 26, the dosing and drying may also take place in graphite tubes without the platform 26.

Image sequences comprised of a plurality of images are recorded with the camera 22 during the insertion of the sample and the atomization. Every image consists of image points which are arranged in lines and columns in the usual way. The image sequences are automatically processed as follows:

A camera of the type 21K155USB-C from the manufacturer Videology Imaging Solutions, Inc. is used as an image source in the present embodiment. The camera uses a CCD-Sensor (Charge-coupled Device) of the type Sony ICX279AK. The sensor effectively has 752×582 image elements, also referred to as an image point with an image point side ratio of 9:10. The image data provided by the camera is transmitted with a resolution of 720×576 image pixels. In Microsoft Windows the camera is addressed via DirectShow. The camera is connected with the computer via USB 2.0.

A direct artificial illumination serves as a light source 28 (FIG. 2) which may be a light emitting diode. It illuminates the interior of the graphite tube 10 mostly homogeneously. In the present embodiment, image information of the graphite tube 10 is analyzed. The visual information is present in the form of an image sequence (video), wherein a video constitutes a sequence of successive images f(x, y). Here, "x" refers to the position of an image pixel in a line and "y" refers to the position of an image pixel in a column. The information content of an individual image is determined, as well as the changes of the image information over the time according to the difference between several images of an image sequence.

The image processing comprises the following steps, which are explained in detail hereinafter:
1. Determining an interesting range of the images
2. Bottom detection
3. Recognizing the pipetting distance of the dosing means
4. Recognizing the complete drying of the sample
5. Recognizing the approaching of the boiling point of the sample
6. Recognizing the type of furnace tube, that is if a platform 26 is present or not.

The necessary image material reaches a computer in the form of a color video data stream. Every image, thereby, consists of image points. In the present case, a color image is based on a red, green and blue color channel. An image point of a color image is defined by a red, green and blue color value. The red, green and blue color information is each represented by 1 Byte (8 Bit). Every color, that is red, green and blue, is represented as an intensity value r, g or b in $2^8=256$ gradations. This results in overall 16,777,216 ($=2^8*2^8*2^8$) displayable colors per image point. In other words: three images; each an image with red R, green G and blue B color information; are transmitted at a time.

For further processing, every color image is converted into an intensity image of grey scales without color. An example of such an intensity image is illustrated in FIG. 7. For converting the images with color information into an intensity image, every image point at the position (x, y) in the image is assigned a grey value $g_{x,y}(r, g, b)$ according to the following formula:

$$g(x,y,R,G,B)=0.2989*R(x,y)+0.5870*G(x,y)+0.1140*B(x,y)$$

With:
R: Intensity value on the image point in the red color channel
G: Intensity value on the image point in the green color channel
B: Intensity value on the image point in the blue color channel
g: Grey scale in the intensity image Then, several intensity images provided in sequence are time averaged for noise reduction. Subsequently, the image evaluation takes place with the time averaged intensity images. The averaging is effected according to:

$$\bar{g}(x, y) = \frac{1}{N}\sum_{i=1}^{N} g_i(x, y, R, G, B)$$

Figure 10:
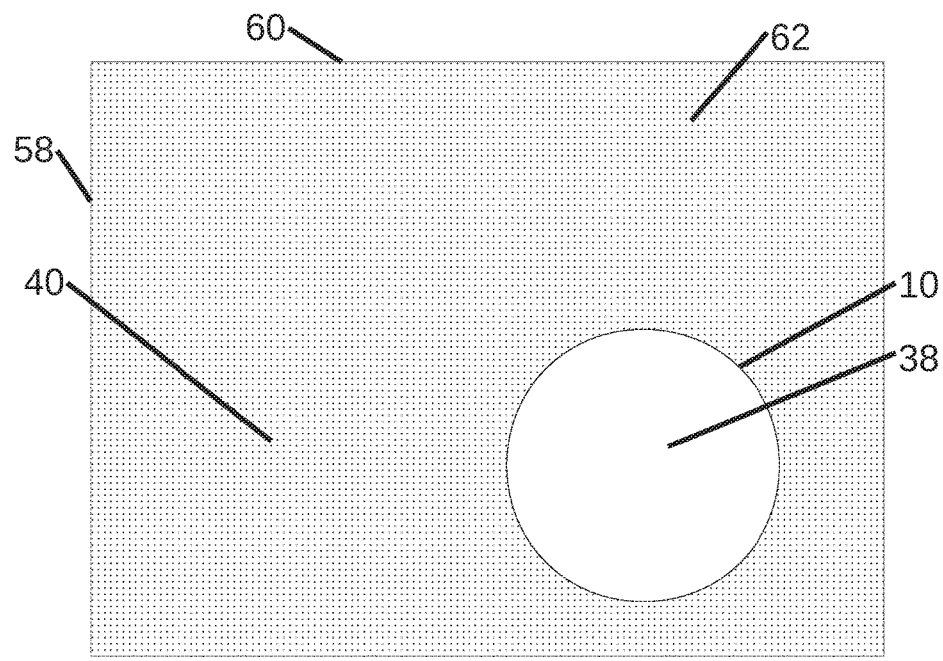
FIG. 10 is a schematic view of an unprocessed image of the graphite tube of FIG. 4 taken with a camera.

With:
x: Position of the image point in a row
y: Position of the image point in a column
N: Total number of images averaged in time
$g_i$: Grey scale of the image point (x,y) in the $i^{th}$ image In the FIGS. 10 and 11, it can be seen that only one subsection 38 is of interest. The graphite tube 10 is displayed in this subsection. The remaining subsection 40 only shows the uninteresting surroundings of the graphite tube 10. The remainder of the images is uninteresting. The size and position of the interesting subsection 38 in the originally recorded image may vary. This depends, among other things, on the adjustment of the camera 22 and the actual device type of the atomic absorption spectrometer.

In order to minimize the computing effort and the computing time for the image analysis algorithms described hereinafter, the uninteresting subsection 40 is separated from the interesting subsection 38 in the image. Thereby, the overall resource consumption, for example, necessary computing power and time is minimized. For this purpose, the uninteresting subsection 40 of an image f(x,y) is removed with a process termed "RoI". Ideally, the resulting image, thereby, only includes the interesting section g(x',y') of the image f(x,y). In the present embodiment, f(x,y) corresponds to the averaged image $\bar{g}(x,y)$.

The following applies to the interesting subsection 38 g(x',y'):

$$g(x',y')=RoI(f(x,y))$$

with
x', y': Position of the image points in the interesting section.
It is: x'≤x and y'≤y.

The uninteresting part 40 of the image is recognizable by the relatively big and homogeneous regions, which range from the border 58 and 60 of the image 62 to the interesting section 38. The intensity of the image points in the uninteresting section 40 ranges from dark grey to black. The interesting part 38 is recognizable in FIG. 11 and can have all kinds of values. Accordingly, the Fourier transformation of the grey values has relatively high frequencies in the interesting part 38, which suggests a strong contrast. In the uninteresting part 40 there are smaller frequency values in the Fourier transformation.

Figure 11:
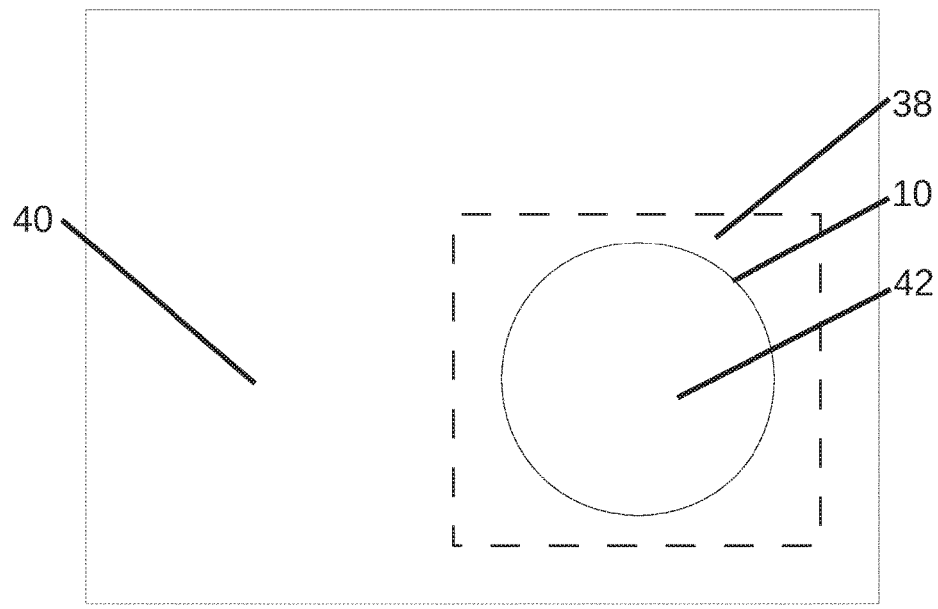
FIG. 11 is a schematic view of the image represented in FIG. 10 after the filtering with an edge detector.

FIG. 11 shows a representation referred to as a "contrast image". The contrast image of an image represents rapid changes of the grey values f of adjacent image points in the image. Image regions 42 with high frequencies are highlighted in a contrast image. In the present case, the edges of the furnace tube wall and the platform, or rather the furnace tube bottom, are highlighted. High frequencies may be highlighted by the application of a high pass filter or with an edge detector.

An example for an edge detector is a Sobel operator. The normalized image consists of values between 0 and 1, wherein 0.0 and 1.0 [0.0, 1.0] are included. The value 0 corresponds to the lowest frequency and 1 complies with the highest frequency.

Figure 12:
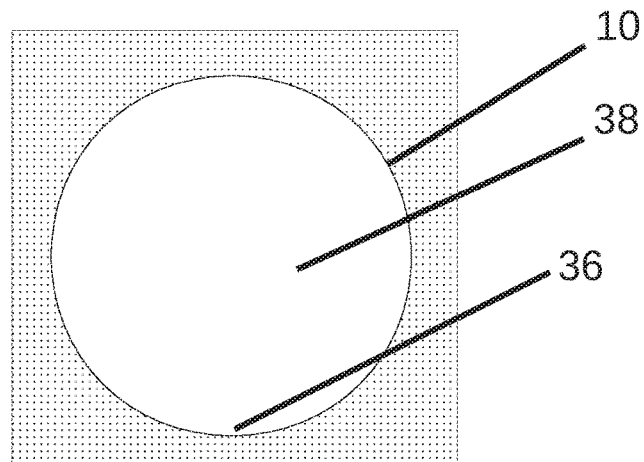
FIG. 12 illustrates the determined region of interest.

The application of a high pass filter to the original image or the averaged image of the camera, causes regions with low frequencies to be masked and regions with high frequencies to be highlighted. This way, the interesting part 38 of the image is separated from the uninteresting part 40. This is illustrated in FIG. 12.

The detection of the bottom 36 or the platform 26 in the graphite tube 10 serves as the basis for the recognition of the pipette 30 and the pipetting distance 64 (FIG. 5) as well as for the recognition of the drying. The optics of the camera 22 is adjusted during the manufacturing of a spectrometer in such a way, that the region of the graphite tube 10 with the opening 16 for the pipette 30 in the graphite tube 10 is in the focal point 24. The adjustment, thereby, is carried out with the pipette 30 inserted into the graphite tube 10. This very focused area 24 of the graphite tube bottom is of importance for the recognition of the pipette 30, its pipetting distance 64 and the drying recognition, since the pipette 30 is inserted and the sample 32 dispensed in this area.

For simple digital compact cameras, the autofocus works by means of contrast measurements. If the focal point is adjusted precisely, the image provides the highest possible contrast. The focal point is determined in the image by the region with the highest contrast, that is the highest frequencies.

Figure 14:
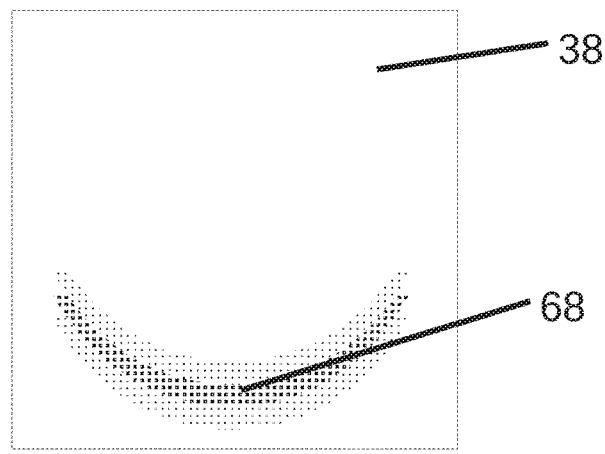
FIG. 14 is a schematic view of the graphite tube with a spatial and frequency resolution.

A contrast image or an image with a spatial and frequency resolution may be created from an image with an empty graphite tube, as it is represented in FIG. 3. This is illustrated in FIG. 14. From this, a model is created as described below, which represents the highest contrasts. If it is possible to fit a function to the model, the resulting function will represent the graphite tube bottom in the range of the focal point 24 in the image.

With the spatial information or rather coordinate of an image point, the frequency information present in this region and the directly surrounding region can be determined in a representation with a spatial and frequency resolution. In the present case, a two-dimensional representation with a spatial and frequency resolution has an approximated spatial resolution, since before, a respective independent fourier transformation was performed in a plurality of subsections of the image.

In order to determine the pipetting distance 64, the pipette 30 in the interior of the graphite tube 10 and its relative position must be recognized. Due to specific variations and manufacturing tolerances, a reference point is necessary for the distance measurement. Upon recognizing the pipette 30 by a difference image analysis according to FIG. 35, the position of the pipette 30 is determined relative to the image borders. In a difference image analysis, a difference image of two images f(x,y) and h(x,y) is created, by subtracting their grey values from one another for every image point. A current image with a pipette is created thereby and a reference image without a pipette is used, like illustrated in FIG. 5 and FIG. 4.

In order to achieve the absolute pipetting distance, a reference point is necessary. In this case, it must be the bottom of the graphite tube, that is designated with 36 in FIG. 3, directly under the inserted pipette 30. It is provided that the pipette and the underlying bottom 36 lie in the focal point 24 of the camera 22.

For the recognition of the completed drying it is determined when a pipetted sample 34 is fully dried during the drying process. It is important for the recognition, that the image or the contrast image of a graphite tube 10 with the dried sample 34 is similar or even identical, depending on nature and type of the sample, to a reference image of the empty graphite tube 10. If the image of the graphite tube 10 with the dried sample 34 and the reference image are identical or resemble each other, the condition of the complete drying may be determined with the difference image analysis. In doing so, a current image with a pipetted sample and a reference image without a sample are compared to each other. Upon the completion of the drying process, both images exhibit only slight differences. The difference image shows no or only minimal structures.

With certain samples, like, for instance, blood, heavy oil or heavily saline solvents, it is possible that the difference image analysis does not provide a satisfactory result. Upon drying of such a sample, the image can deviate at the corresponding position in the graphite tube 10 from the empty graphite tube 10, due to drying residuals 34. In this case, a structural image difference is present despite the complete drying. Hence, the difference image analysis is not sufficient on its own for such samples. Another possibility is to carry out the recognition of the complete drying on the basis of the contrast. Instead of a contrast image, an image with a spatial and frequency resolution can also be used for this, as illustrated in FIG. 14. In doing so, the current image is transferred to a corresponding representation. The contrast images of an image without a sample and an image with a sample not yet dried, generally differ from each other. The more the sample approaches the complete drying during the drying phase, the more similar the contrast images will become.

Figure 17:
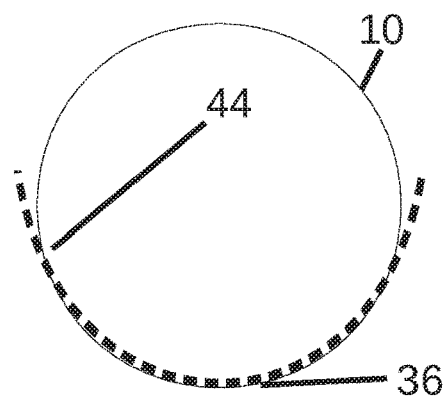
FIG. 17 is a schematic view of the graphite tube with a recognized bottom.
Figure 18:
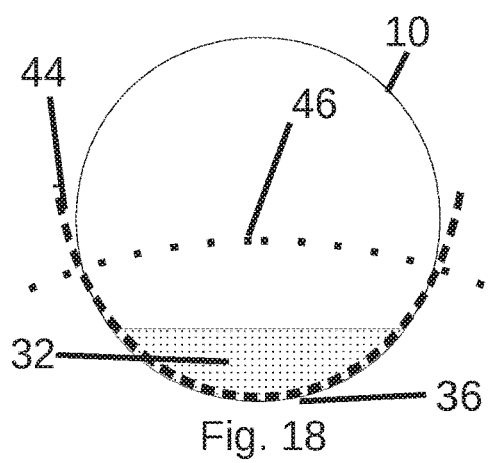
FIG. 18 is a schematic view of the graphite tube with a sample and the function, which represents the current horizontal course of the region of the highest contrast.
Figure 19:
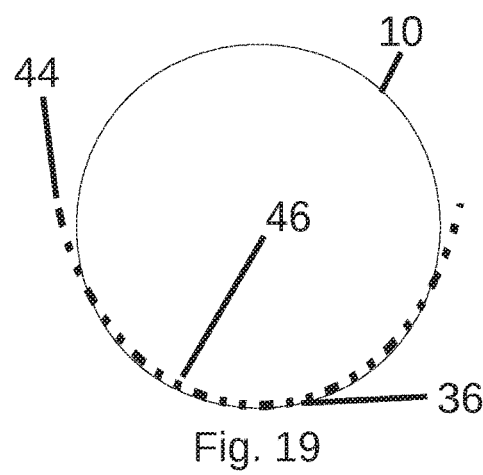
FIG. 19 is a schematic view of the dried graphite tube, where the superimposition of the functions of FIGS. 17 and 18 indicates the completed drying process.

In order to recognize the complete drying by means of the contrast, a reference image is necessary. In the present embodiment, the reference image is a contrast image of an empty graphite tube without a pipetted sample. During the drying, a contrast image is created for every image provided by the camera 22. After the contrast image is created, it is compared to the reference image. If the comparison results in an overall correspondence, it can be assumed that the sample 34 is dried like it is illustrated in FIG. 9. The result of the bottom detection described above, is used for the comparison. The bottom detection of the graphite tube 10 is based on the evaluation of a contrast image. The contrast image provides a related function with the bottom detection, which is illustrated in FIG. 17. The bottom detection will provide roughly the same results before the pipetting the sample 32 into the empty interior of the graphite tube 10 and after the drying the sample 34. This is illustrated in FIG. 19. During the drying phase illustrated in FIG. 18, the sample 32 is located in liquid form on the bottom 36 of the graphite tube or rather on the platform 26, which leads to an apparent deviation.

The approaching of the boiling temperature is apparent by the formation of bubbles 48 in and on the sample. The bubbles are illustrated in FIG. 8. Objects in the form of bubbles 48 stand out clearly from their surroundings, thanks to the direct illumination of the graphite tube 10. In contrast to their surroundings, these objects 48 have a relatively high intensity.

In order to filter out corresponding objects 48, the Laplacian of Gaussian method, also known as the Marr-Hildreth-Operator or the Difference of Gaussian method, is applied in the present embodiment. The methods are commonly known, for example, from the publication by Roman Glebov indicated in the section "Prior Art" or from the internet at http://www.cs.unc.edu/~lazebnik/spring11/lec08_blob.pdf and https://en.wikipedia.org/wiki/Blob_detection and therefore do not need to be described any further here.

When applying one of these methods, objects with an intensity distribution similar to the Gaussian function are distinguished the most. This way, rotationally symmetric objects which have a local maximum and a specific scaling, are particularly emphasized. The size in which the objects are highlighted, is controlled by means of scaling the Gaussian function. The bubbles 48 on the sample surface are spherically formed. Due to the lighting, their intensity course in the image is similar to the Gaussian curve. The bubbles may be emphasized by applying the Laplacian of Gaussian or rather the Difference of Gaussian method. Because the objects differ in size, the Laplacian of Gaussian- or Difference of Gaussian methods are performed with different scales.

The Laplacian of Gaussian- or Gaussian method highlights possible candidates for the sought objects and narrows down the choice of possible objects. The candidates refer to sought objects in the form of bubbles that are selected according to false-positive hits and according to correct-positive hits.

The selection can take place with various methods. It is important that the objects are relatively small compared to the overall image. Despite the flat viewing angle, they appear to be nearly circular.

The following approaches are considered:
1. Detecting cone-shaped, rotation symmetrical objects. These have a circular base area. The intensity distribution of the candidates is analyzed and chosen accordingly.
2. Comparing the circumference of the candidate with its area and corresponding selection.

For the implementation of this embodiment, an intensity image of the three color channels is created at first, as described above. Every image sequence made up of several images of the graphite tube sequentially provided by the camera is time averaged for noise reduction.

The image has a high contrast in the interesting region 38 compared to the uninteresting region 40. For separation, a Sobel operator is used for recognizing high frequencies. Regions with high frequencies are thereby highlighted in the image and regions with low frequencies are suppressed.

The Sobel operator belongs to the category of the edge detector filters. The filter is applied to an image by convolution and, in doing so, calculates an approximation of the first derivative. Thereby, a gradient image is created from the intensity image. Regions with abrupt intensity changes and the corresponding high frequencies in the Fourier transformation, are assigned high values and vice versa. High frequencies are highlighted. The Sobel Operator only acts in one coordinate direction. Every image is, therefore, filtered twice: once with the Sobel operator and once with a transposed Sobel operator.

Figure 36:
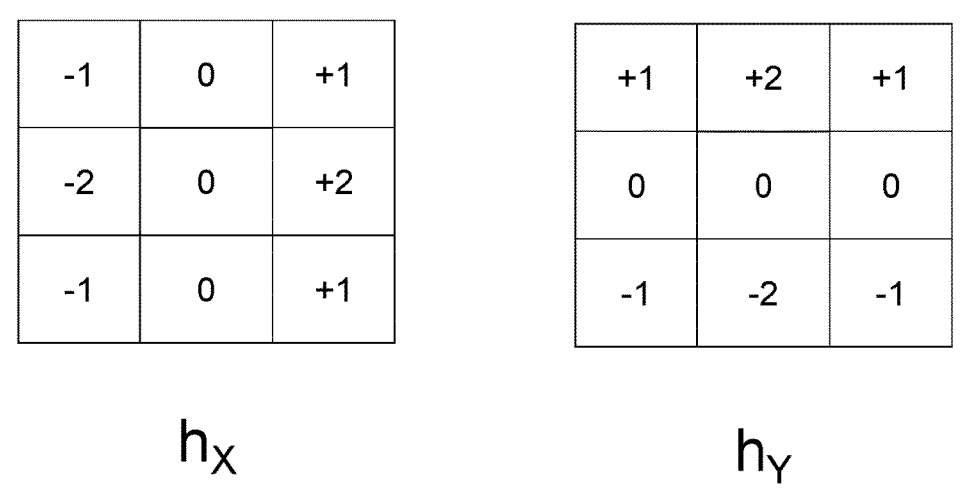

The applied Sobel operator is illustrated in FIG. 36 and is described further at https://de.wikipedia.org/w/index.php?title=Sobel-Operator&oldid=128396157_. The Sobel operator is applied twice on the input image by convolution. The first application relates to vertical ($h_X(x,y)$) and the second application to horizontal ($h_Y(x,y)$) structures in the image. The Sobel operator is thereby rotated by 90 degrees.

By means of a threshold value, the result f'(x, y) is transferred into a binary image b(x, y). The threshold value is selected in such a way that, ideally, only the region of interest 38 has elements with the value 1 and the remaining elements generally only have the value 0. By determining the elements with 1, the maximum dimensions and the position of the region of interest is determined by means of their positions. The region of interest g(x, y) is separated from the uninteresting region by the dimensions and the position of the region of interest relative to the entire image f(x, y). In the horizontal x-axis, the smallest ($x_{min}$) and the largest ($x_{max}$) x-coordinate of all elements with the value 1 define the borders of the region of interest on the x-axis. Likewise, the smallest ($y_{min}$) and the largest ($y_{max}$) y-coordinate of the elements with the value 1 define the borders of the region of interest on the y-axis (vertical axis). The overall result of this method are 4 coordinates $x_{min}$, $x_{max}$, $y_{min}$, $y_{max}$, which describe the position of the region of interest 38 in FIG. 11 relative to the overall image.

In summary, the algorithm may be represented as follows:
1. Intensity image f(x, y) with the original measurements, filtering by convolution with the Sobel operator ($h_X(x,y)$ and $h_Y(x,y)$).

$$i(x,y) = f(x,y) \otimes h_X(x,y)$$

$$j(x,y) = f(x,y) \otimes h_Y(x,y)$$

$$f'(x,y) = \sqrt{i^2(x,y) + j^2(x,y)}$$

2. Transferring the result f'(x,y) of the filtering into a binary image b(x,y), by means of a threshold value n.

$$b(x, y) = \begin{cases} 0, & \text{if } f'(x, y) < n \\ 1, & \text{if } f'(x, y) \geq n \end{cases}$$

3. Determining of the position of the elements with the value 1 in the binary image b(x, y).
4. Defining the limits of the subsection in consideration of these positions $x_{min}$, $x_{max}$, $y_{min}$, $y_{max}$, wherein $$X \subseteq \mathbb{N} \text{ (Set of the image elements in } X - \text{Dimension)}$$

$$Y \subseteq \mathbb{N} \text{ (Set of the image elements in } Y - \text{Dimension)}$$

$$S^2 \subseteq X \times Y \text{(interesting subsection of the image)}$$

$$(x, y) \in X \times Y$$

$$x_{min}, x_{max} \in X$$

$$y_{min}, y_{max} \in Y$$

$$u(x, y) = \begin{cases} 1, & \text{if } \exists x'(x' \in X \wedge b(x', y) = 1) \wedge \exists y'(y' \in Y \wedge b(x, y') = 1) \\ 0, & \text{otherwise} \end{cases}$$

-continued $$[x_{min}, x_{max}] \times [y_{min}, y_{max}] :=$$
$$\{(x', y') \in S^2 \mid (x_{min} \leq x' \leq x_{max}, y_{min} \leq y' \leq y_{max}) \wedge u(x', y') = 1\}$$

As described above, the detection of the bottom 36 of the platform 26 in the graphite tube 10 will then follow. The bottom detection is based on the evaluation of an intensity image f(x,y), which represents the empty graphite tube 10. This is shown in FIG. 3. For this purpose, the color image with the empty graphite tube must be re-converted into an intensity image for the interesting region 38, as described above.

At the start of the bottom detection, the image f(x, y) is filtered with a high pass filter $h_p(x,y)$, as illustrated in FIG. 12. For performance reasons, this is carried out by means of a Fourier transformation in the frequency domain by a multiplication with the filter. However, it is also possible to perform a convolution in the spatial domain. An alternative option is to convert the image f(x, y) into a representation with a spatial and frequency resolution. The representation g(x,y) is the result.

Figure 13:
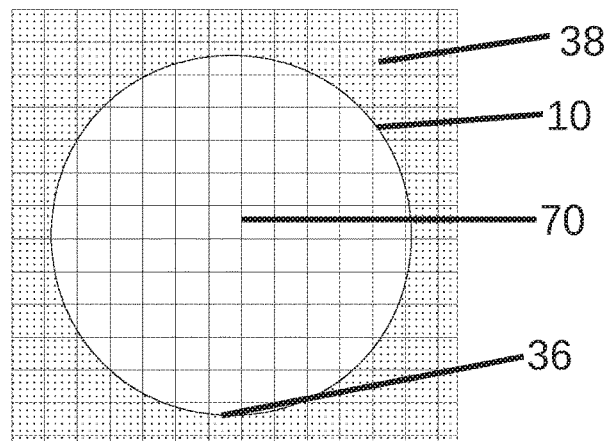
FIG. 13 is a schematic view of the graphite tube with quadratic tiles.

A method for creating a representation with a spatial and frequency resolution, as shown in FIG. 14, is based on the subdivision of the input image into small, preferably square subsections 70, which are arranged in lines and columns. This is shown in FIG. 13. A plurality of single image points are provided in every subsection 70. Every single partial image 70 is subsequently transferred by Fourier transformation into the frequency domain. Every element is represented by a complex number. The intensity of every element of a subsection 70, indicates the frequency parts that occur in the partial image in the frequency domain. A relatively high intensity represents high frequencies. A relatively low intensity stands for low frequencies in the corresponding part of the image. The accuracy of the method depends on the size of the subsections 70. The smaller the subsections 70, the more exact will the method be. For the bottom detection, this method yields good results in a simple way. An example 68 is illustrated in FIG. 14.

Figure 15:
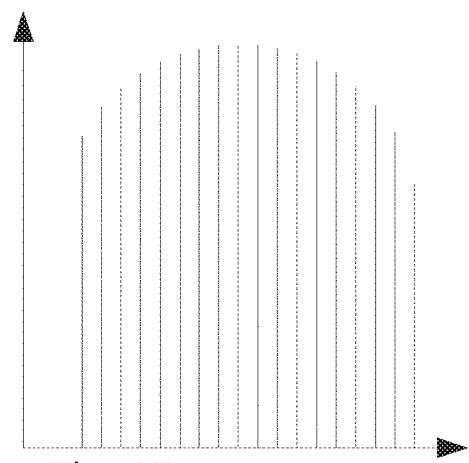
FIG. 15 is a schematic view of the horizontally mirrored bottom model of the graphite tube.
Figure 16:
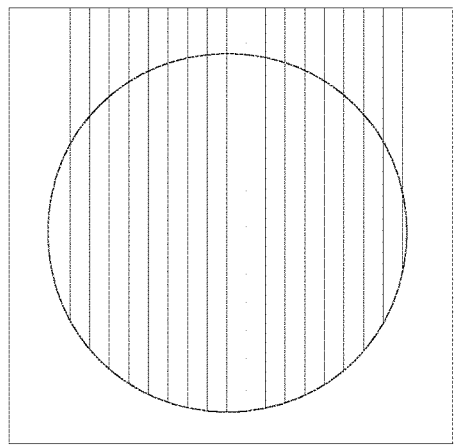
FIG. 16 is a superimposed, schematic view of the bottom model with the graphite tube.

The bottom detection is based on a representation g(x, y) of the image with a spatial and frequency resolution. With the help of this representation, the bottom 36 of the graphite tube 10 or the platform 26 is determined. In the next step, a model is created which represents the highest frequencies in the representation g(x, y). This is illustrated in FIGS. 15 and 16. In every column of the representation g(x, y), the highest value is taken and the corresponding position of the value in this column is transferred into a vector. This way the number of the vector elements of the model M is determined by the number of columns in the representation g(x, y). Every element n of the vector thereby comprises the y-coordinate of the image point with the highest intensity in the column n of the representation g(x, y). Thus, the second entry of the model vector has, for example, the value 5. This means that the highest frequency and the highest contrast is present in the second column in the region of the fifth element, or rather of the image point of the representation g(x, y).

$$X \subseteq \mathbb{N}$$
$$Y \subseteq \mathbb{N}$$
$$P \subseteq \mathbb{R}$$

-continued $$g: X \times Y \to P$$
$$maxPos: X \to Y$$
$$maxPos(x) := \{y \in Y \mid \forall r \in P: r \leq g(x, y)\}$$
$$T \subset X$$
$$U = X \setminus T$$
$$T = [x\_min, x\_max] := \{x \in X \mid (x\_min \leq x \leq x\_max) \wedge \exists a \in U :=$$
$$((a\langle x_{min} \vee a\rangle x_{max}) \wedge maxPos(a) = 0)\}$$

$$M = \begin{bmatrix} maxPos(x_{min}) \\ maxPos(x_{min} + 1) \\ \vdots \\ maxPos(x_{max} - 1) \\ maxPos(x_{max}) \end{bmatrix}$$

The result of the entries in the model vector already represents, among other things, the bottom 36 or the platform 26. This is represented in FIG. 16. However, it cannot be derived where the bottom is limited in the horizontal alignment, since further structures present in the image disturb this recognition. Furthermore, the model includes a noise component. For this reason, the model is further processed as follows. The model M (bottom) of the graphite tube 10 can be roughly expressed by a quadratic function. In the next step, a function is fitted to the model. By means of an equalization calculus, a polynomial bottom(x), for example of the second degree, is fitted to the model. Moreover, by fitting the function to the model, the beginning and the ending of the graphite tube in the image can also be determined. Outliers and noise in the original model may be reduced by the fitting. In addition to this, disturbing structures outside of the graphite tube, i.e. left and right of the graphite tube, are removed. The function is fitted as follows by means of iterative elimination of outliers according to the 3-Sigma criterion, wherein:

$$P\{|M-E(M)|<3\sigma\}=0.9973$$
$$\hookrightarrow P\{E(M)-3\sigma<M<E(M)+3\sigma\}=0.9973$$

After fitting, the standard deviation to the model values is determined. Model values that lie outside of the threefold standard deviation, are removed from the model. The elimination of the outliers is applied to each new model, until there are no more outliers present.

After the elimination of outliers, the bottom 36 of the graphite tube or the platform 26, is represented by the fitted function 44. This is illustrated in FIG. 17. Furthermore, it can be derived by means of the model M, in which the outliers were eliminated, where the bottom 36 of the graphite tube or the platform 26 begins ($x_{min}$) and ends ($x_{max}$) in the horizontal (x-axis).

Summarizing the method:
1. Filtering the intensity image f(x, y) of the empty graphite tube with a high pass filter $h_p(x, y)$ or converting it into a representation with spatial and frequency resolution. The result is g(x, y).
2. Seeking the highest value in every column in g(x, y) and inserting the corresponding position into a vector. The vector represents a model, wherein the vector has as many elements as the representation g(x, y) has columns.
3. A polynomial bottom(x) is fitted to the model by means of iterative elimination of outliers according to the 3-sigma criterion. The limit of the bottom is thereby also determined.

For the purpose of determining the pipetting distance 64, the deepest position of the pipette 30 and, as a reference point, the position of the bottom 36 lying underneath it or the platform 26, are required. Therefore, the pipette 30 and bottom 36 or the platform 26 must each be recognized on the basis of image information. The pipette 30 is recognized by means of a difference image analysis. In doing so, the current image, for example from FIG. 5, is compared to a reference image, for example FIG. 4. For the purpose of the difference image analysis, the reference image h(x, y) and the current image with a pipette f(x, y) are present in the form of an intensity image.

Figure 35:
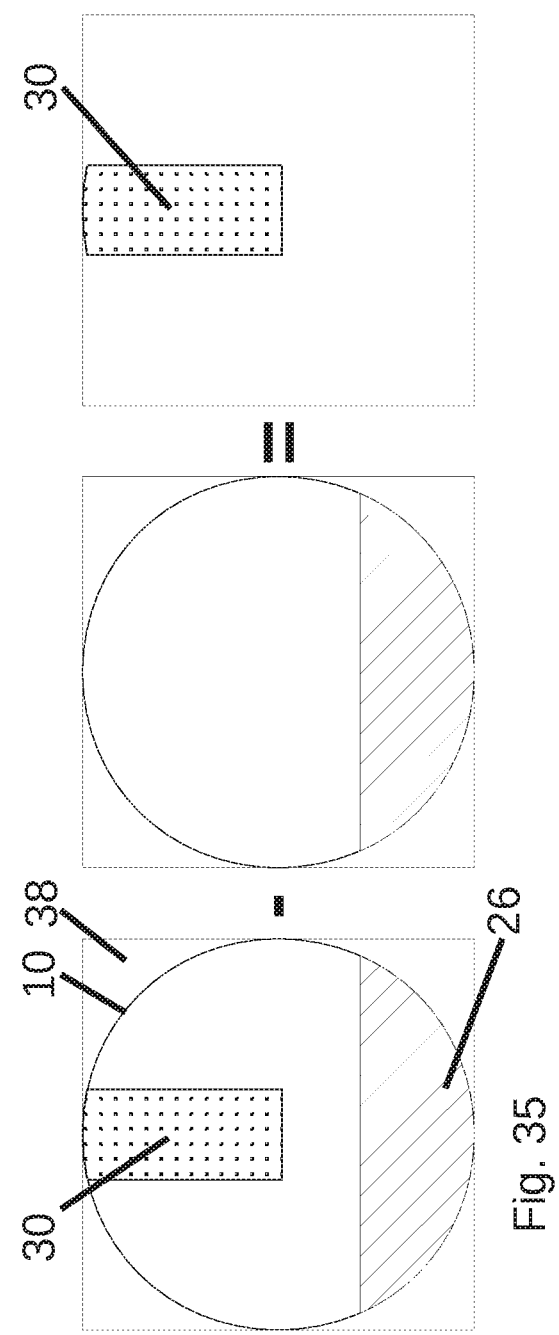
FIG. 35 illustrates how the condition of the pipette inserted into the graphite tube is determined by calculating the difference between a reference image of the empty graphite tube and a current image of the graphite tube with an inserted pipette.

The resulting difference image g(x, y) includes all differences between both input images. This is illustrated in FIG. 35. Apart from minimal differences in the entire image due to noise, it is, in this case, primarily the pipette 30. By comparison, the difference values of the pipette 30 are greater than the differences created by noise. The pipette 30 is separated from the noise by means of a suitably selected threshold value. The position of the pipette 30 is then determined. This includes the left border 74, the right border 76 and the lower limit 78 of the pipette 30. The coordinates x and y are normalized to unity relative to the image dimensions and added to a feature vector. In addition to this, the feature vector includes the width 80 of the pipette.

If the feature vector lies within the given limitations, the modification in the image is confirmed to be the pipette. This is also called a classification. The limit values are thereby set manually. Alternatively, the limit values may also be learned.

In order to determine the distance 64 between the pipette 30 and the bottom 36 or the platform 26, the position of the bottom is first detected as described above. A polynomial bottom(x) is fitted to the bottom 36 of the graphite tube 10 or of the platform 26.

The pipetting distance 64 of the pipette 30 may be calculated by means of the function 44 adapted to the bottom 36 or to the platform 26 and the position of the pipette 30 in the image. To that end, the difference of the lowest pipetting position and the highest point of the bottom 36, or the platform 26, is formed under the pipette 30. The pipetting distance 64 is the result.

The method briefly summarized:
1. recognizing the pipette 30 and its position in the image by means of the difference image analysis.
2. determining the position of the bottom 36 or the platform 26 underneath the pipette 30 by means of bottom detection.
3. computing the pipetting distance 64 by means of the pipetting position in the image and the bottom position of the graphite tube 10.

The recognition of the complete drying is primarily based on the comparison of contrast images or of representations with spatial and frequency resolution with the help of the bottom detection explained above. Every current image, for example the graphite tube with the sample, is compared to the reference image. In addition to this, the recognition can also be carried out by means of a difference image analysis.

The current image and the reference image are each first converted into an intensity image. Subsequently, the intensity images are separately processed with the previously described bottom detection. This determines a function 44, as it is illustrated in FIG. 17. Such a function 44 is, for example, a polynomial. The function 44 represents the bottom 36 of the graphite tube 10 or the platform 26. The function 44 has a steady course right across the delivered image, for example, from left to right. In the case of the reference image, the function 44 represents the actual course of the bottom 36 of the graphite tube 10 or the platform 26. The course of the bottom (function 46) of the current image varies according to the image contents. This is illustrated in FIG. 18. The further the drying process of the sample proceeds, the more similar to the reference function 44 and the bottom 36 or the platform 26, the course of the function 46 of the current image will be.

As soon as the functions 44 and 46 are identical or nearly identical, as illustrated in FIG. 19, the sample 34 is considered to be dried up. The similarity is determined by reaching a threshold value. The functions are compared by means of their coefficients. The comparison always refers to a threshold value. According to the specific application, the "comparison" either refers to the direct evaluation of a value with a threshold value, the subtraction, or the euclidean distance between vectors as a coefficient comparison. However, a formation of quotients may also be used as a coefficient comparison. Subsequently, the difference, the distance or the quotient are, where applicable, evaluated by means of a threshold value. In the present embodiment, the coefficients of a function are interpreted as a vector. Their euclidean distance is determined on the basis of both vectors. If the euclidean distance is smaller or the same as a defined threshold value $S_{Acceptance1}$, both functions are considered to be sufficiently similar. In order to increase the accuracy, the comparison is performed and reviewed several times in a row, whether the suitable corresponding result is being created. Only then the sample 32 on the bottom 36 or the platform 26 is classified as being completely dried.

The current images of the graphite tube are continuously evaluated during the drying phase.

Also, the recognition of the complete drying by means of a difference image analysis is possible. The current image f(x,y) is compared in the same way with the reference image h(x,y) during the drying process. The current camera image is referred to as f(x,y), the reference image is referred to as h(x,y) and the comparative result is:

$$g(x,y)=|f(x,y)-h(x,y)|$$

The result g(x, y) is represented in FIG. 20 and includes all differences between both input images. The differences, apart from minimal differences, due to noise are essentially the differences in the entire image in relation to the current drying progress. With a suitable threshold value $S_{Noise}$, the noise is removed from the difference image and, therefore, only represents the significant differences.

If there are no longer any differences present and the difference image only consists of zero entries, the bottom is considered to be dry. The situation is represented in FIG. 21. Even if the difference image represents only few differences in regard to a further predefined threshold value $S_{Acceptance2}$, the bottom is considered to be dry. For reasons of reliability, the comparison must also provide the corresponding result several times in a row so that the bottom is considered to be completely dry.

The second method by means of a difference image analysis of the drying recognition, supports the above illustrated first method, which is based on bottom detection. The overall accuracy improves under the following condition: The sample that is to be dried may leave behind no or almost no visually recognizable residuals, that is particles that are captured by the camera due to their size, so that the difference image analysis can provide reliable results. Furthermore, by applying both methods the time period from the actual drying in the graphite tube to the recognition of the drying may be reduced by the algorithm.

When samples are dried which leave behind visually recognizable residuals 34 after drying, the second method cannot be used. As per description, the second method does possibly not provide a useable result with such samples. In this case, only the first method with the bottom detection can be used, since it provides a reliable result regardless of the sample.

The recognition shortly summarized:
1. Method contrast image analysis:
   a) Assigning a function (polynomial) to the reference image by means of bottom detection.
   b) Assigning a function (polynomial) to the current image by means of bottom detection.
   c) Comparing the coefficients of both functions by means of the euclidean distance. If the distance is smaller than the threshold value $S_{Acceptance1}$, the sample is considered to be dried.
2. Method difference image analysis:
   a) Calculating the difference g(x, y) of the current image f(x, y) and the reference image h(x, y).
   b) Removing the noise in g(x, y) with the threshold value $S_{Noise}$.
   c) Classifying the bottom as dried or not dried by means of the threshold value $S_{Acceptance2}$.

The approaching of the boiling point of the sample is recognized by the occurrence of bubbles 48. This is illustrated in FIG. 8. Bubbles 48 are exposed from the rest of the sample 32 due to their relatively high intensity. The entire method can generally be viewed as a feature detector for rotationally symmetric objects in an image. During the drying phase of the sample 32, images of the camera 22 are continuously evaluated. Regardless of applied methods, potentially occurring bubbles 48 must be highlighted at the beginning. The method Difference of Gaussian is used in this implementation. Because this method is continuously applied to the incoming intensity images, the corresponding filter kernels are created with different scalings at the beginning. For this purpose, a series of filter kernels is generated, which are subject to certain conditions. For every possible combination of sets $Q_1 \subset \mathbb{R}$ und $Q_2 \subset \mathbb{R}$, a filter kernel is generated, wherein $\sigma_1 \in Q_1$, $\sigma_2 \in Q_2$ und $\sigma_1 > \sigma_2$.

The current intensity image is then filtered in the frequency domain with every generated filter kernel. Every filter result $g_n(x, y)$ may include information on the objects 48 in the corresponding scaling stage ($\sigma_1$ and $\sigma_2$). The effectivity may be illustrated well by means of the Gaussian pyramid. In doing so, several scaling stages of the intensity images are created. The filter result is the difference between two selected scaling stages of the intensity images. All filter results are then combined to one result g(x, y).

For this purpose, the largest value at every point (x, y) is taken in all filter results $g_n(x, y)$ and adopted to the result g(x, y) at the positions (x, y). All possible candidates for bubbles are highlighted in the overall result g(x, y). The negative values are generally disregarded, since they are of no importance for this method. The candidates must be selected for the objects 48 by a suitable method.

In general, the recognition of almost circular objects by means of a Hough-Transformation is possible. However, due to the small sizes of the bubbles, this is not possible in the present case.

$$g(x, y) = \max_n g_n(x, y)$$

Various methods are possible:
Method 1

The first method is based on the detection of conic and rotationally symmetric objects. Conic objects are hereby highlights and non-conic objects masked or damped. The intensity of an element of the overall result g(x, y) is not used as an intensity, but as a coordinate for a third axis (z-axis).

For reasons of efficiency, a preselection is carried out for possible candidates in the overall result g(x,y). Everything below the simple standard deviation $1*\sigma$ of g(x, y) is disregarded. The intermediate result $z_W(x,y)$ is hereby created. In the second step, all local maxima in $z_W(x, y)$ are taken and considered as new possible candidates. Up to this point, the approach to the recognition of the approaching of the boiling point of the sample is based on the application of the Difference of Gaussian-Method with different scalings, on an input image and on the filtering of local maxima.

With the above illustrated method, all result images are joined to form an overall result and the maxima detection is subsequently performed on this two-dimensional result.

Due to the preselection of the possible candidates, only the positions where possible candidates are present need to be filtered in the following step of the method, rather than the entire image g(x,y).

Figure 22:
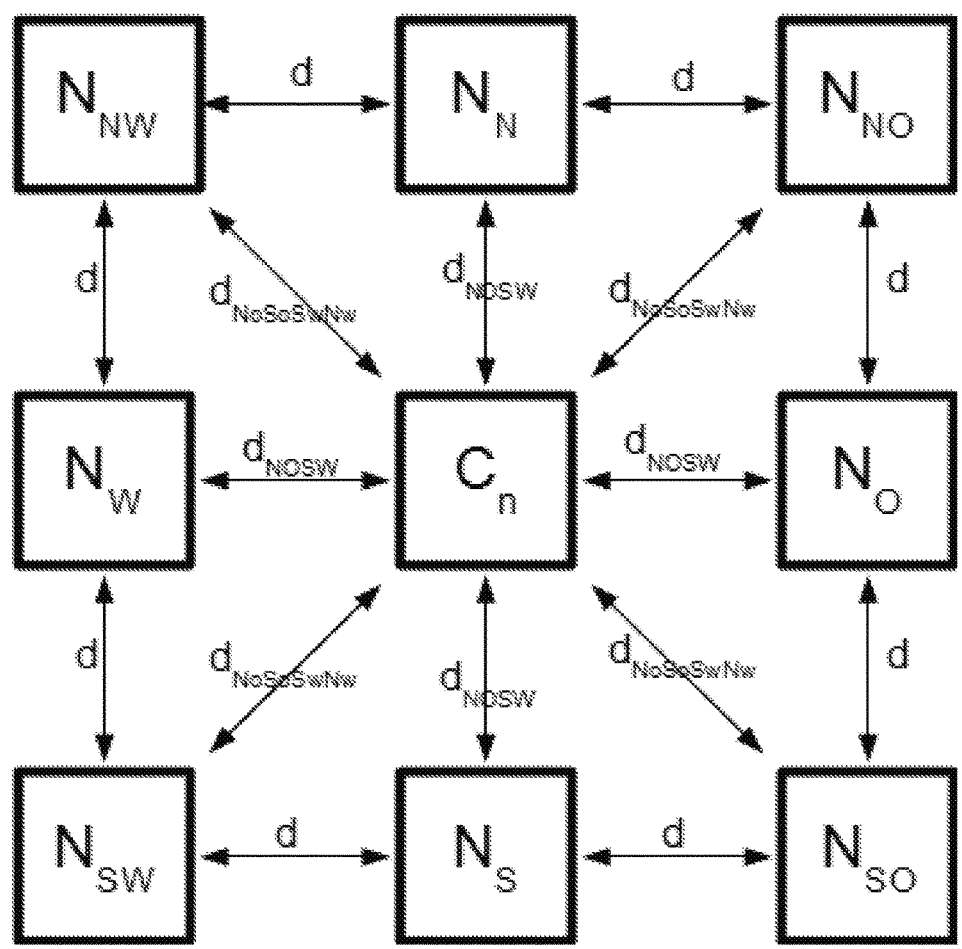
FIG. 22 is a schematic view of the gradient operator and a representation of the distances from the origin to its neighbors.

A non-linear filtering is applied. For a candidate $C_n$ the gradient regarding each of eight not necessarily adjacent neighbors is calculated. The neighbors are located directly in the north, east, south, west, northeast, southeast, southwest and northwest direction in relation to the candidates. The four neighbors north, east, south and west have the same distance $d_{NESW}$ to the candidate. This is illustrated in FIG. 22. The neighbors in the directions of northeast, southeast, southwest and northwest also have the same distance $d_{NeSeSwNw}$ to the candidate. If the distance d is given, then the north, east, south and west neighbors have a distance to the candidates of $$d_{NESW} = d$$

Northeast, southeast, southwest and northwest neighbors have a distance to the candidates of $$d_{NeSeSwNw} = \sqrt{2d^2}.$$

The approach presented so far is similar to the monotony operator by Zimmermann and Koris, which is described in "Eine Familie von Bildmerkmalen für die Bewegungsbestimmung in Bildfolgen" in: Zimmermann, G.; Kories, R.: Mustererkennung 1984. Bd. 87. Springer-Verlag GmbH, 1984, S. 147-153.

According to this, the standard deviation $\sigma_{NESW}$ is calculated by means of a multiple K of the gradient of the neighbors north, east, south and west. It must be noted that the security of the value of the standard deviation is fuzzy, since only a very small sample size is present. Subsequently, the standard deviation $\sigma_{NeSeSwNw}$ is calculated for the multiple K of the gradient northeast, southeast, southwest and northwest. The standard deviations are calculated separately because the corresponding neighbors have different distances to the actual candidates ($d_{NESW} \neq d_{NeSeSwNw}$). The coefficient K is a predetermined value, wherein it is K>1.

Because the calculation of the standard deviation ($\sigma_{NESW}$ and $\sigma_{NeSeSwNw}$) is relatively computationally intensive, the maximum absolute deviation from the mean value ($maxDiff_{NESW}$ and $maxDiff_{NeSeSwNw}$) of the given values is calculated as an alternative. In order to conclude the filtering at the candidate $C_n$, the sum $\sigma_{NESW}+\sigma_{NeSeSwNw}$ or maxDiff$_{NESW}$+maxDiff$_{NeSeSwNw}$ is subtracted from the value $z_W(x, y)$ at the position of $C_n$ and written into a new matrix sol.

The standard deviation $\sigma_g$ is calculated from the overall result $g(x, y)$ after the matrix sol is filled with the values of all candidates. All candidates in the matrix sol for which the values are larger than $N*\sigma_g$ refer to bubbles 48. N is hereby set to be an indirect threshold value, wherein it is N>1.

The Summary of method 1:
1. Preselection of the candidates in the overall result $g(x,y)$ by means of taking all local maxima in $g(x,y)$, every maximum represents a potential candidate.
2. For each candidate:
    a) Calculating the gradient in distance $d_{NeSeSwNw}$ and $d_{NeSeSwNw}$ to its neighbors.
    b) Calculating the standard deviation ($\sigma_{NESW}$ und $\sigma_{NeSeSwNw}$) or the maximal absolute deviation from the mean value (maxDiff$_{NESW}$ and maxDiff$_{NeSeSwNw}$) via the gradients separately for north-east-south-west and northeast-southeast-southwest-northwest.
    c) The sum $\sigma_{NESW}+\sigma_{NeSeSwNw}$ or maxDiff$_{NESW}$+maxDiff$_{NeSeSwNw}$ is subtracted from the actual candidate value in the matrix $z_W(x,y)$ and written into the matrix sol at the same position.
3. Calculating the standard deviation $\sigma_g$ of the overall result $g(x, y)$.
4. All candidates in the matrix sol larger $N*\sigma_g$, refer to bubbles.

Method 2

The second method is based on the detection of nearly circular objects 50. For this purpose, the candidates are selected based on the relation between the circumference and the area. If corresponding candidates are recognized as nearly circular, they refer to bubbles 48. The intensity of an element of the overall result is thereby used as a coordinate for a third axis (z-axis).

The standard deviation $\sigma_g$ of $g(x,y)$ is determined at the beginning. A given multiple N of $\sigma_g$ serves as a threshold value for a further preselection of candidates. Potential candidates in $g(x,y)$ must have a larger value than $N*\sigma_g$.

$$K:=\{(x,y)|x,y \in \mathbb{N} \wedge (g(x,y)>N*\sigma_g)\}$$

Figure 23:
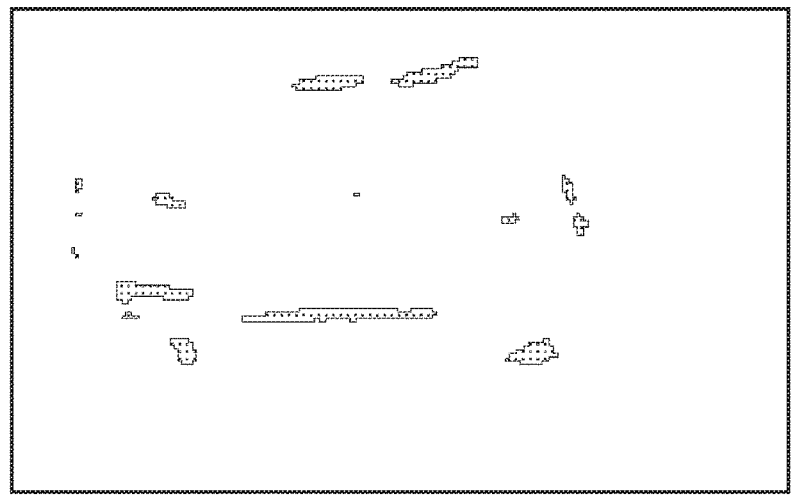
FIG. 23 shows a sectional view of the interior of the graphite tube during the drying process with the N-fold standard deviation N*σ.

After that, the circumference is compared to the area for all present candidates for the first time in the cutting plane at $N*\sigma_g$ of FIG. 23. For this purpose, the circumference U and the area A is determined of every present candidate. By means of the circumference U, the area $A_{Circle}$ of a circle corresponding with the circumference is calculated on the basis of image points. A is compared to $A_{Circle}$ with a given threshold value $S_{Acceptance}$. If the absolute difference $|A-A_{Circle}|$ is larger than the threshold value $S_{Acceptance}$, than the candidate is a false-positive hit and is disregarded.

It is:

$$U=2\pi r$$

$$A=\pi r^2$$

Figure 24:
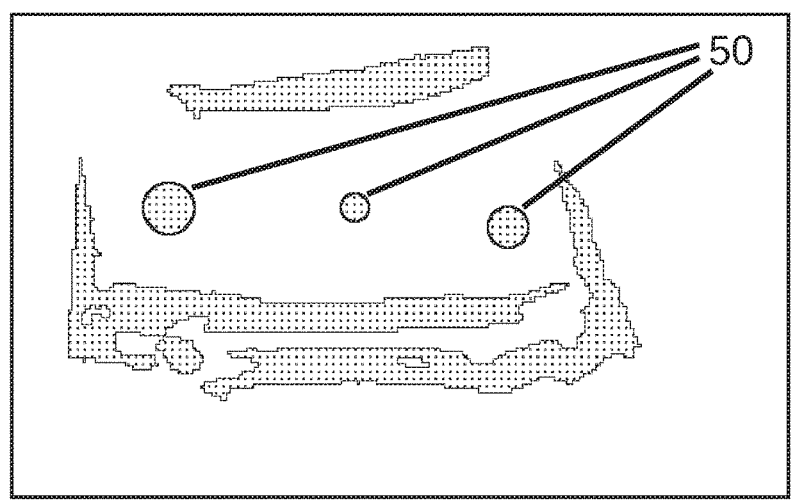
FIG. 24 corresponds to the sectional view of FIG. 23 with a simple standard deviation 1*σ.
Figure 25:
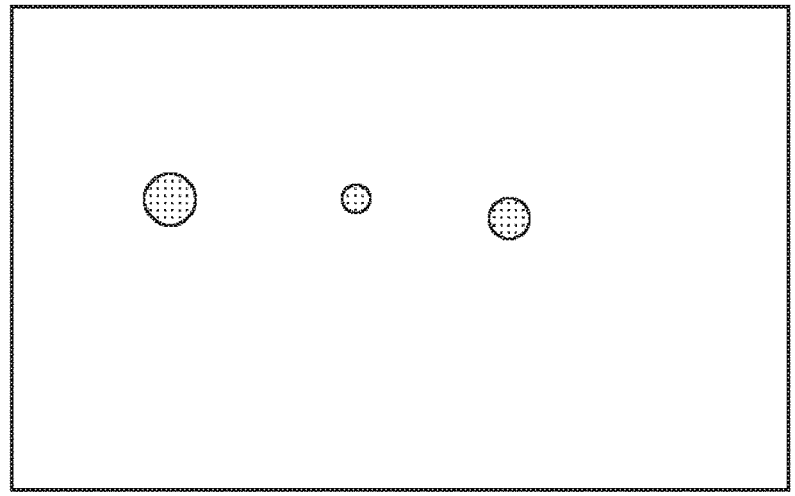
FIG. 25 corresponds to the sectional view of FIGS. 23 and 24 which only shows recognized bubbles.

The same method is performed again with the remaining candidates at $1*\sigma_g$. This is recognisable in the cutting plane at $1*\sigma_g$ in FIG. 24. All remaining candidates that are recognizable in FIG. 25 refer to correct-positive hits, thus truly recognized bubbles 48.

The summary of the method:
1. Determining the standard deviation $\sigma_g$ of the overall result $g(x, y)$.
2. Only candidates with the value in $g(x, y)$ larger than $N*\sigma_g$ are considered any further:
3. For every candidate larger than $N*\sigma_g$:
    a) The circumference U and the area A of the candidates in the cutting plane at $N*\sigma_g$ are determined.
    b) The area $A_{Circle}$ of a corresponding circle is calculated to the circumference U.
    c) Calculating the difference $|A-A_{Circle}|$. If the difference is larger than the threshold value $S_{Acceptance}$, than the candidate is disregarded.
4. For every candidate still remaining:
    a) The circumference U and the area A of the candidates are determined in the cutting plane at $1*\sigma_g$.
    b) The area $A_{Circle}$ of a corresponding circle is calculated to the circumference U.
    c) Calculating the difference $|A-A_{Circle}|$. If the difference is larger than the threshold value $S_{Acceptance}$, than the candidate is disregarded.
5. All remaining candidates are bubbles.

Figure 26:
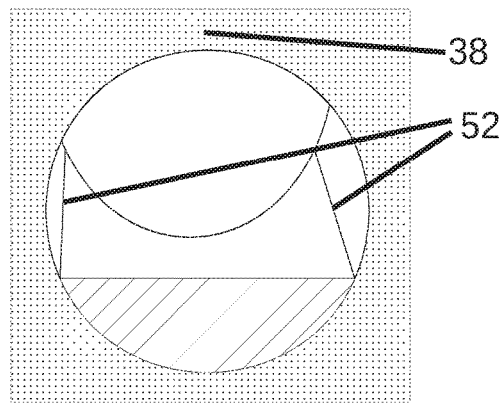
FIG. 26 illustrates the graphite tube with a L'vov platform with necessary details for edge detection and the subsequent mask generation.
Figure 28:
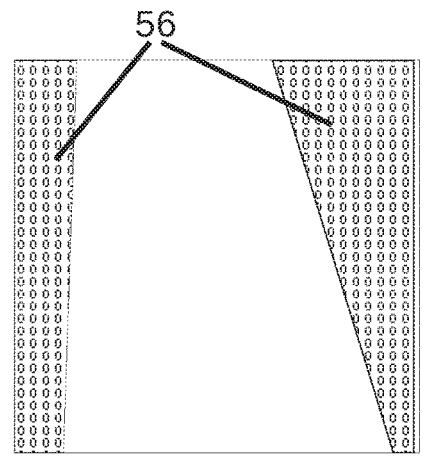
FIG. 28 shows the mask created by means of the edge detector.
Figure 29:
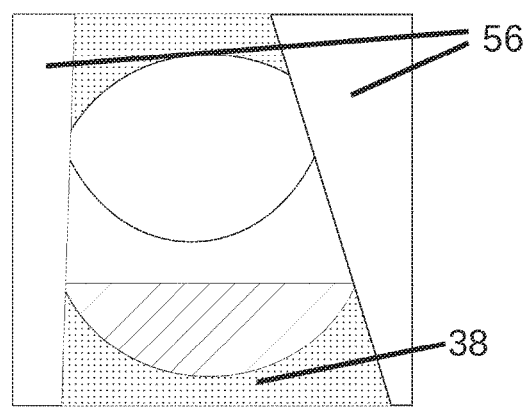
FIG. 29 shows the graphite tube of FIG. 26 after the masking of uninteresting regions by superimposition with the generated mask.
Figure 30:
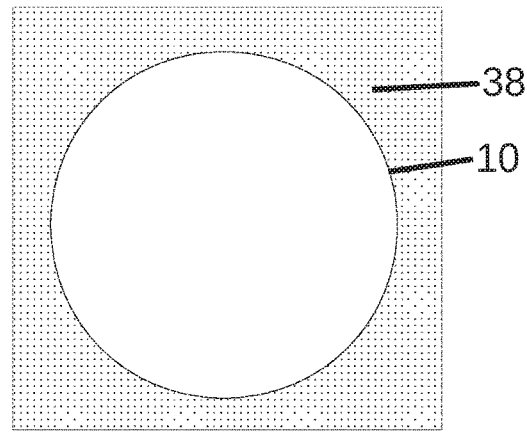
FIG. 30 illustrates the graphite tube without a L'vov platform, where the mask generation is based on the determination of the convex wrapping.
Figure 33:
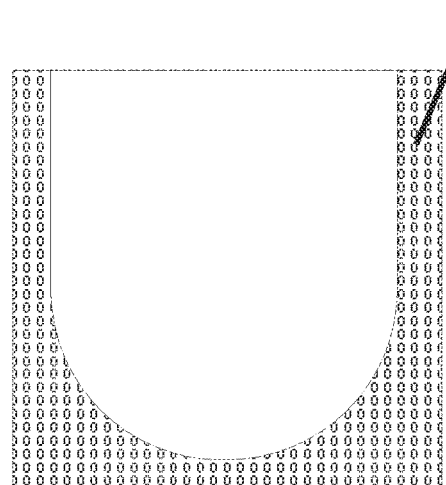
FIG. 33 final, upwardly opened mask for a graphite tube without a L'vov platform.

In order to improve the runtime of the above described methods, a mask is created, which marks the region outside of the tube. This is illustrated in FIG. 28 and FIG. 33. A mask 56 superimposed with the current image of FIG. 26 with the furnace and platform is, for example, illustrated in FIG. 29. Every image point in that region is set to zero therein. This is illustrated in FIG. 28 and FIG. 33. Both detection methods thereby ignore this region. For this purpose, the structure of the graphite tube must be known. Two graphite tubes exist, on the one hand a graphite tube with a platform as illustrated in FIG. 26, on the other hand, a graphite tube without a platform. This is illustrated in FIG. 30. The graphite tube with the platform has distinctive edges 52 at the left and right border of the platform. In addition to this, relatively strong contrasts are located at the left and right border of the graphite tube 10, due to the direct graphite tube illumination. With the graphite tube without a platform, contrasts are only recognizable at the left and right border of the graphite tube, due to the direct graphite tube illumination.

Accordingly, corresponding edges in the image should be detectable. In order to create the mask, an image of the empty and unpipetted graphite tube space is required at first. This is illustrated in FIG. 26. The original color image of the camera is used, which is provided by the camera driver. The color image is smoothed with a Gaussian low-pass filter in order to minimize noise. The color image is present in the RGB color space, with three color channels existing for red, green and blue.

Figure 27:
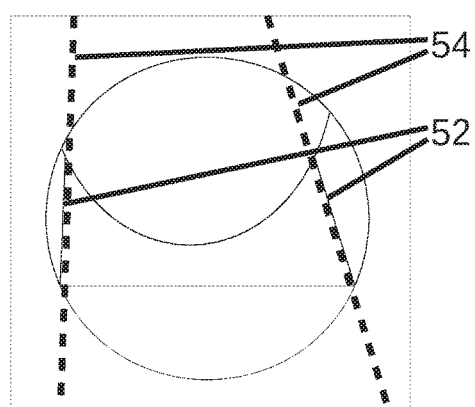
FIG. 27 shows the graphite tube of FIG. 26 after the filtering with an edge detector and the recognition of important edges.

Subsequently, an edge detection is performed for the color green ($f_B$ (x, y)) by means of the intensity image of the channel, with the help of the Sobel operator. The intensity image is filtered with the Sobel operator $h_X(x, y)$ and $h_Y(x, y)$ $$i(x,y)=f_B(x,y) \otimes h_X(x,y)$$

$$j(x,y)=f_B(x,y) \otimes h_Y(x,y)$$

$$f'(x,y)=\sqrt{i^2(x,y)+j^2(x,y)}$$

and converted to a binary image with a given threshold value $S_{BW}$ thereafter. On the basis of the binary image, a Hough transformation is applied for straight lines. The result is an accumulation of the straight lines 54 (FIG. 27) assigned to the edges 52, wherein the straight lines are present in the parametric form. The entire process is also performed with the blue color channel, which also leads to detected straight lines in the image. The color image of the graphite tube includes valuable information primarily in the green and blue color channel. The red color channel is ignored for this reason.

Subsequently, the detected straight lines are compared with each other and uninteresting straight lines are sorted out. This occurs on the basis of knowledge, which exists on the geometry of the graphite tube. Ultimately, those candidates that mark the left and right border of the graphite tube are maintained. The region outside of the detected edges defines the mask 56. This corresponds to the region outside of the graphite tube, which is recognizable in FIG. 28. Uninteresting regions of the graphite tube FIG. 26 are masked in FIG. 29 by means of superimposition with the created mask 56 FIG. 28. This works reliably with the graphite tube with a platform. With the graphite tube without a platform, this approach does not lead to the intended result, since the distinctive edges of the platform are not present. The mask would cover parts of the field of vision of the graphite tube, due to incorrect straight line detection. As a result, it is indirectly possible to identify the kind of graphite tube and determine whether a platform is present or not. From this, new applications of the method illustrated here may be derived.

Figure 31:
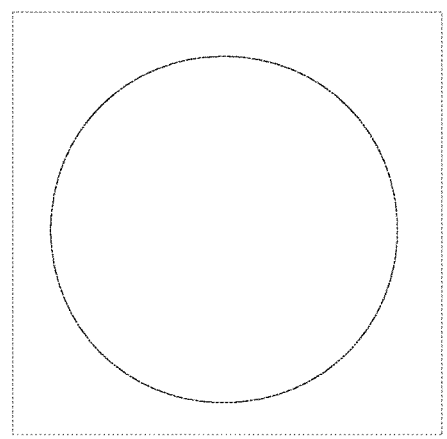
FIG. 31 shows the FIG. 30 after the filtering with an edge detector, only the edge of the graphite tube is recognizable.
Figure 32:
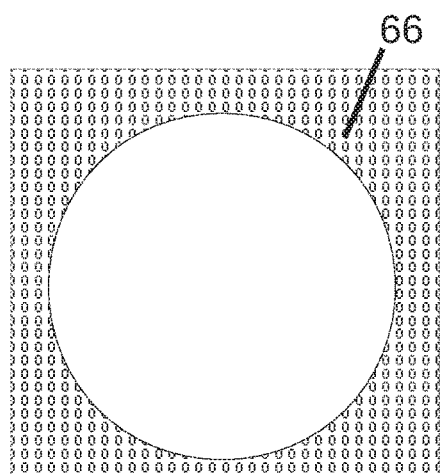
FIG. 32 shows the provisional mask generated by means of the convex wrapping.
Figure 34:
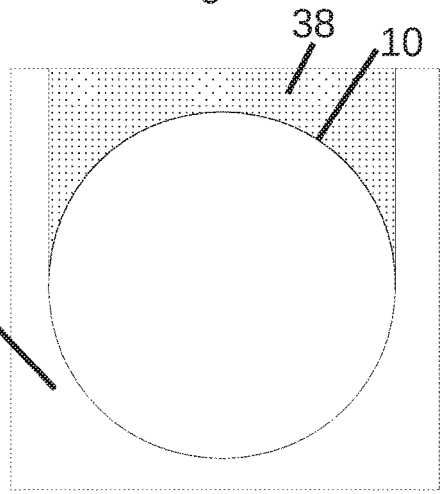
FIG. 34 shows the graphite tube of FIG. 30 after the masking of uninteresting regions by superimposition with the generated mask, FIG. 33.

Because the created mask is not applicable for graphite tubes without a platform, the mask is created by other means. The edge detection is performed by means of the Sobel operator on all three color channels of the initial graphite tube image of FIG. 30. Subsequently, the convex wrapping is created on the basis of the three edge images of FIG. 31. The convex wrappings of all three channels are superimposed thereafter and then form the new, provisional mask 66. This is illustrated in FIG. 32. The total amount of all convex wrappings and the region above the total amount, result in the new mask 58. This is represented in FIG. 33. In FIG. 34, uninteresting regions of the graphite tube of FIG. 30 are masked by means of superimposition with the created mask 58 of FIG. 33.

What is claimed is:

1. A method for the spectral analysis of samples in a graphite tube, said graphite tube having a temperature, comprising the steps of:
    (a) inserting a liquid sample into a graphite tube having an interior;
    (b) drying said sample by heating said graphite tube;
    (c) transferring said sample into a particle cloud by further heating up said graphite tube thereby generating optical signals or providing optical signals influencing conditions in said particle cloud; and
    (d) measuring one of said optical signals influenced or generated by said sample in said particle cloud with a detector;
    wherein
    (e) image sequences of images of said interior of said graphite tube are recorded with a two-dimensional camera having a plurality of image elements over selected periods of time for spectral analysis, wherein the optical path of the camera does not influence the optical path of said optical signals measured with said detector;
    (f) said images of said image sequences are automatically processed with image processing methods;
    (g) a reference image of said interior of said graphite tube is determined;
    (h) the condition of said graphite tube, of said sample and/or of a dosing means for the inserting said sample into said graphite tube is determined by comparison of said images of said image sequences to said reference image; and
    (i) wherein said temperature of said graphite tube is controlled depending on said condition or depending on parameters which describe said condition.

2. The method of claim 1, and wherein a following step of said spectral analysis is triggered when a selected target state is reached.

3. The method of claim 1, and wherein the images of said image sequences are processed only for one section which is the same for all images of said image sequences.

4. The method of claim 3, and further comprising the steps:
    (a) filtering an intensity image f(x, y) with the original dimensions by means of folding with a Sobel operator ($h_x(x,y)$ and $h_y(x,y)$), wherein $i(x,y)=f(x,y) \otimes h_x(x,y)$ $j(x,y)=f(x,y) \otimes h_y(x,y)$ $f'(x,y)=\sqrt{i^2(x,y)+j^2(x,y)}$ with x, y: coordinates of the image points
    (b) transferring the results f' (x, y) of the filtering into a binary image b(x, y) with a threshold n according to the rule:

$$b(x,y) = \begin{cases} 0, & \text{if } f'(x,y) < n \\ 1, & \text{if } f'(x,y) \geq n \end{cases}$$

(c) determining the position of the elements with the value 1 in the binary image b(x, y);
    (d) limiting the subsection in consideration of these positions $x_{min}$, $x_{max}$, $y_{min}$, $y_{max}$, wherein $X \subseteq \mathbb{N}$ (set of the image elements in $X$ – Dimension)

$Y \subseteq \mathbb{N}$ (set of the image elements in $Y$ – Dimension)

$S^2 \subseteq X \times Y$ (interestin subsection of the image)

$(x, y) \in X \times Y$ $x_{min}, x_{max} \in X$ $y_{min}, y_{max} \in Y$ $$u(x,y) = \begin{cases} 1, & \text{if } \quad \exists x'(x' \in X \wedge b(x', y) = 1) \wedge \exists y'(y' \in Y \wedge b(x, y') = 1) \\ 0, & \text{otherwise} \end{cases}$$

$[x_{min}, x_{max}] \times [y_{min}, y_{max}] :=$ $\{(x', y') \in S^2 \mid (x_{min} \leq x' \leq x_{max}, y_{min} \leq y' \leq y_{max}) \wedge u(x', y') = 1\}$.

5. The method of claim 1, and wherein the position of said graphite tube or the position of parts of said graphite tube or the position of a platform arranged in said graphite tube, are automatically determined with said image processing means.

6. The method of claim 5, and wherein the position is determined by the following steps:
    (a) filtering said intensity image f(x, y) of the empty graphite tube with a high pass filter or converting said intensity image f(x, y) into a representation with spatial and frequency resolution to a filtered image g(x, y); wherein the frequency information present in this area is determined in a representation with a spatial and frequency resolution via the spatial information in the form of coordinates, (b) determining the highest value in every column of g(x,y) and inserting the corresponding position in a vector so that the vector represents a model, wherein the vector has as many elements as there are columns in the representation g(x, y), (c) performing an iterative elimination of outliers according to the 3-Sigma criterion and adapting a polynomial to the model, wherein $P\{|M-E(M)|<3\sigma\}=0.9973$ $P\{E(M)-3\sigma<M<E(M)+3\sigma\}=0.9973$ (d) determining the desired position $X \subseteq \mathbb{N}$ $Y \subseteq \mathbb{N}$ $P \subseteq \mathbb{R}$ $g: X \times Y \to P$ $maxPos: X \to Y$ $maxPos(x) := \{y \in Y \mid \forall r \in P : r \leq g(x, y)\}$ $T \subset X$ $U = X \setminus T$ $T = [x\_min, x\_max] := \{x \in X \mid (x\_min \leq x \leq x\_max) \wedge \exists a \in U :=$ $((a \langle x_{min} \vee a \rangle x_{max}) \wedge maxPos(a) = 0)\}$ $$M = \begin{bmatrix} maxPos(x_{min}) \\ maxPos(x_{min}+1) \\ \vdots \\ maxPos(x_{max}-1) \\ maxPos(x_{max}) \end{bmatrix}.$$

7. The method of claim 5, and wherein the position and/or the pipetting distance of a dosing means for the insertion of said sample into said graphite tube is automatically determined with said image processing means.

8. The method of claim 7, and wherein the determination is effected by the following steps:
(a) recognition of the pipette and its position in said image by means of the difference image analysis in relation to said reference image by forming the difference between said image and said reference image;
Pipetting position in the interval $pipX_{min} \ldots pipX_{max}$ und $pipY_{min} \ldots pipY_{max}$
(b) determining the position and/or the relative level of the bottom below the pipette to the image border via the bottom detection; via a polynomial bottom(x) and the position of the bottom with the shortest distance to the pipette $$PositionY_{Bottom}(\text{begin}, \text{end}) = \min_{x=\text{begin}}^{\text{end}} (\text{bottom}(x))$$

(c) calculating the pipetting distance by means of the pipetting position in said image and the bottom position of said graphite tube, wherein Distance=$|PositionY_{Bottom}(pipX_{min},pipX_{max})-pipY_{max}|$.

9. The method of claim 1, and wherein the reaching of the complete drying of said sample is automatically determined with said image processing means.

10. The method of claim 9, and wherein the reaching complete drying is determined by the steps:
(a) determining a function in said reference image, preferably of a polynomial, by means of bottom detection, wherein the function describes the course of the highest contrast in said image with horizontal alignment,
(b) for each current image determining a function in in the current image, preferably of a polynomial, by means of bottom detection;
(c) comparing both functions by means of Euclidean distance of the coefficients and determining said image, where the distance is smaller than a threshold value.

11. The method of claim 9, and wherein the reaching of the complete drying is determined by the steps:
(a) forming the difference g(x, y) between each current image f(x, y) and said reference image h(x, y);
(b) removing the noise in g(x, y) by comparison with a threshold value;
(c) determining said image, where the value is smaller than the threshold value.

12. The method of claim 1, and wherein the presence and/or the position of bubbles is automatically determined during the drying of said sample with said image processing means.

13. The method of claim 12, and wherein the determination is carried out by the following steps:
(a) preselection of the candidates of possible bubbles represented by the positions (x, y) in the overall result g(x, y) by searching for all local maxima, wherein every maximum represents a potential candidate;
(b) for each candidate:
  I) calculating the increase in distance to its neighbors $d_{NESW}$ and $d_{NeSeSwNw}$;
  ii) calculating the standard deviation ($\sigma_{NESW}$ and $\sigma_{NeSeSwNw}$) or the maximum absolute deviation from the average value (maxDiff$_{NESW}$ and maxDiff$_{NeSeSwNw}$) via the increases separately for north-east-south-west and northeast-southeast-southwest-northwest;
  iii) forming the difference of the actual candidate value in the matrix $z_W(x,y)$ and the sum $\sigma_{NESW}+\sigma_{NeSeSwNw}$, or rather, maxDiff$_{NESW}$+maxDiff$_{NeSeSwNw}$, the difference in the matrix sol is subsequently written down at the same position;
(c) calculating the standard deviation $\sigma_g$ of the overall result g(x, y);
(d) defining all candidates in the matrix sol larger $N*\sigma_g$ than bubbles.

14. The method of claim 12, and wherein the determination is carried out by the following steps:
(a) determining the standard deviation $\sigma_g$ of the overall result g(x, y);
(b) disregarding of all values except the candidates with the value in g(x, y) larger than $N*\sigma_g$;
(c) for every candidate with a value larger than $N*\sigma_g$:
  i) determining the circumference U in the cross section at $N*\sigma_g$ and of the area A of the candidates;
  ii) calculating the area $A_{Circle}$ of a circle corresponding to the circumference;
  iii) calculating the difference $|A-A_{circle}|$ and disregarding all candidates, where the difference is larger than the threshold value $S_{Acceptance}$;
(d) for every candidate still present:
  i) determining the circumference U in the cross section at $1*\sigma_g$ and of the area A of the candidates;
  ii) calculating the area $A_{Circle}$ of a circle corresponding to the circumference;

iii) calculating the difference $|A-A_{Circle}|$ and disregarding all candidates, where the difference is larger than the threshold value $S_{Acceptance}$;

(e) defining all candidates still present as bubbles.

15. The method of claim 1, and wherein optimized values and parameters are developed for the analysis process for further use by means of the condition determined with said image processing means.

16. The method of claim 1, and wherein a mask is generated.

17. The method of claim 1, and wherein it is determined, which graphite tube type is present.

* * * * *